US009605031B2

(12) United States Patent
Gelbart et al.

(10) Patent No.: US 9,605,031 B2
(45) Date of Patent: Mar. 28, 2017

(54) IN VITRO RECONSTITUTED PLANT VIRUS CAPSIDS FOR DELIVERING RNA GENES TO MAMMALIAN CELLS

(71) Applicant: The Regents of the University of California, Oakland, CA (US)

(72) Inventors: William M. Gelbart, Los Angeles, CA (US); Charles M. Knobler, Los Angeles, CA (US); Rees F. Garmann, Santa Cruz, CA (US); Odisse Azizgolshani, Whittier, CA (US); Ruben D. Cadena-Nava, Ensenada (MX)

(73) Assignee: The Regents of the University of California, Oakland, CA (US)

(*) Notice: Subject to any disclaimer, the term of this patent is extended or adjusted under 35 U.S.C. 154(b) by 0 days.

(21) Appl. No.: 14/540,816

(22) Filed: Nov. 13, 2014

(65) Prior Publication Data

US 2015/0140663 A1    May 21, 2015

Related U.S. Application Data

(60) Provisional application No. 61/906,061, filed on Nov. 19, 2013.

(51) Int. Cl.
*C07K 14/005* (2006.01)
*C12N 7/04* (2006.01)
*C12N 5/00* (2006.01)

(52) U.S. Cl.
CPC ............ *C07K 14/005* (2013.01); *C12N 7/045* (2013.01); *C12N 2770/14022* (2013.01); *C12N 2770/14023* (2013.01); *C12N 2770/14042* (2013.01)

(58) Field of Classification Search
CPC ........... C12N 2770/14023; C12N 2770/14042; C12N 2795/18123; C12N 9/127; C12N 2710/10342; A61K 2039/5258; A61K 2039/53; A61K 38/168; C12Y 207/07006
See application file for complete search history.

(56) References Cited

U.S. PATENT DOCUMENTS

2012/0015899 A1* 1/2012 Lomonossoff ....... C07K 14/005
514/49

OTHER PUBLICATIONS

Annamalai et al. Virology, 2005, vol. 332, Issue 2, pp. 650-658.*
Ruden D. Cadena-Nova et al. Journal of Virology, Mar. 2012, vol. 86, No. 6, pp. 3318-3326.*
Mahraj, Payal D. et al. "Nanoparticle encapsidation of Flock House virus by auto assembly of Tobacco Mosaic virus coat protein", International Journal of Molecular Sciences, 15, 2014.
Smith, Mark L. "Assembly of trans-encapsidated recombinant viral vectors engineered from Tobacco mosaic virus and Semliki Forest virus and their evaluation as immunogens", Virology 358, 321-333, 2007.

* cited by examiner

*Primary Examiner* — Bao Li
(74) *Attorney, Agent, or Firm* — Gates & Cooper LLP

(57) ABSTRACT

The invention provides compositions of matter comprising a cowpea chlorotic mottle virus capsid protein (CCMV CP) and a ribonucleic acid, as well as methods for using such compositions. In such compositions, the cowpea chlorotic mottle virus capsid protein envelops the ribonucleic acid so as to for a capsid that can inhibit the degradation of the ribonucleic acid (e.g. by RNAses). A method of delivering a ribonucleic acid into the cytoplasm of a mammalian cell is also provided. Typically, the method comprises the steps of combining the mammalian cell with a composition of matter described herein under conditions selected to allow the cowpea chlorotic mottle virus capsid to contact the mammalian cell and deliver the ribonucleic acid into the cytoplasm of a mammalian cell.

8 Claims, 14 Drawing Sheets

All lengths and sequences of RNA, from 100nt to 10,000 nt, can be *completely* packaged by CCMV capsid protein CP), *if* the CP:RNA mass ratio is high enough This *threshold* mass ratio (6:1) is the same for *all* RNA lengths, corresponding to ≈ 10 CP per 100nt
- + 10 charges/CP N-terminus
- -1 charge/nt

*I.e., this ("magic") ratio involves matching the RNA charge with the N-terminal capsid protein (CP) charge.*

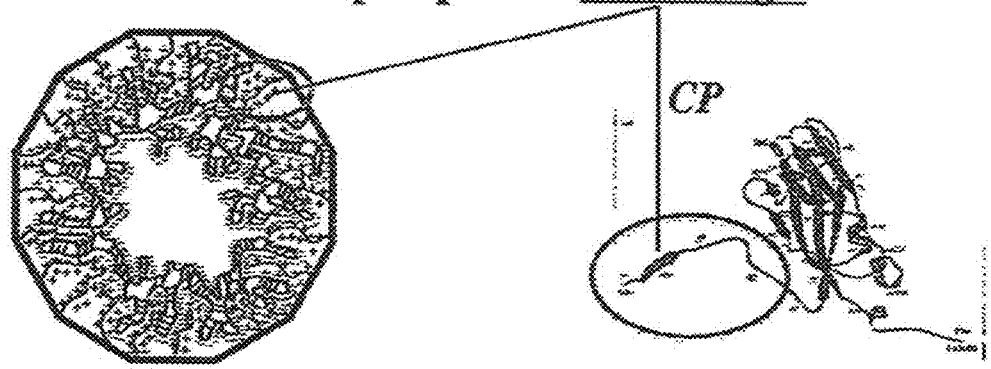

Electrostatic interactions are dominant in driving virus and VLP assembly....

FIG. 9

*In vitro*-reconstituted CCMV VLPs can be wrapped *in vitro* by bilayer membrane, to make enveloped virus-like particles (EVLPs) for gene and vaccine delivery TEM of CCMV capsids (containing the DNA oligo agonist for Herpes vaccine) wrapped by a neutral/cationic lipid membrane

FIG. 14

SEQUENCE LISTING

```
<160> NUMBER OF SEQ ID NOS: 2

<210> SEQ ID NO 1
<211> LENGTH: 190
<212> TYPE: PRT
<213> ORGANISM: Cowpea chlorotic mottle virus
<220> FEATURE:
<223> OTHER INFORMATION: capsid protein

<400> SEQUENCE: 1

Met Ser Thr Val Gly Thr Gly Lys Leu Thr Arg Ala Gln Arg Arg Ala
1               5                   10                  15

Ala Ala Arg Lys Asn Lys Arg Asn Thr Arg Val Val Gln Pro Val Ile
            20                  25                  30

Val Glu Pro Ile Ala Ser Gly Gln Gly Lys Ala Ile Lys Ala Trp Thr
```

```
                35                  40                  45
Gly Tyr Ser Val Ser Lys Trp Thr Ala Ser Cys Ala Ala Glu Ala
    50                  55                  60

Lys Val Thr Ser Ala Ile Thr Ile Ser Leu Pro Asn Glu Leu Ser Ser
65                  70                  75                  80

Glu Arg Asn Lys Gln Leu Lys Val Gly Arg Val Leu Leu Trp Leu Gly
                85                  90                  95

Leu Leu Pro Ser Val Ser Gly Thr Val Lys Ser Cys Val Thr Glu Thr
                100                 105                 110

Gln Thr Thr Ala Ala Ala Ser Phe Gln Val Ala Leu Ala Val Ala Asp
            115                 120                 125

Asn Ser Lys Asp Val Val Ala Ala Met Tyr Pro Glu Ala Phe Lys Gly
            130                 135                 140

Ile Thr Leu Glu Gln Leu Thr Ala Asp Leu Thr Ile Tyr Leu Tyr Ser
145                 150                 155                 160

Ser Ala Ala Leu Thr Glu Gly Asp Val Ile Val His Leu Glu Val Glu
                165                 170                 175

His Val Arg Pro Thr Phe Asp Asp Ser Phe Thr Pro Val Tyr
                180                 185                 190

<210> SEQ ID NO 2
<211> LENGTH: 127
<212> TYPE: RNA
<213> ORGANISM: Tobacco mosaic virus
<220> FEATURE:
<223> OTHER INFORMATION: origin of assembly

<400> SEQUENCE: 2
guuugagaga gaagauuaca aacgugagag acggagggcc cauggaacuu acagaagaag        60
ucguugauga guucauggaa gaugucccua ugucgaucag gcuugcaaag uuucgaucuc       120
gaaccgg                                                                 127
```

IN VITRO RECONSTITUTED PLANT VIRUS CAPSIDS FOR DELIVERING RNA GENES TO MAMMALIAN CELLS

CROSS REFERENCE TO RELATED APPLICATIONS

This application claims the benefit under 35 U.S.C. Section 119(e) of co-pending U.S. Provisional Patent Application Ser. No. 61/906,061, titled "IN VITRO RECONSTITUTED PLANT VIRUS CAPSIDS FOR DELIVERING RNA GENES TO MAMMALIAN CELLS" filed Nov. 19, 2013, the contents of which are incorporated herein by reference.

STATEMENT AS TO RIGHTS TO INVENTIONS MADE UNDER FEDERALLY SPONSORED RESEARCH AND DEVELOPMENT

This invention was made with Government support under Grant Number CHE1051507, awarded by the National Science Foundation. The Government has certain rights in the invention.

SEQUENCE LISTING

The instant application contains a Sequence Listing which has been submitted electronically in ASCII format and is hereby incorporated by reference in its entirety. Said ASCII copy, created on Jan. 30, 2015, is named 30435.277-US-U1_SL.txt and is 2,508 bytes in size.

TECHNICAL FIELD

The present invention relates generally to gene delivery and more particularly, methods and compositions related to the delivery of ribonucleic acid to mammalian cells.

BACKGROUND OF THE INVENTION

The use of animal virus-like particles (VLPs) as vectors for the delivery of genes to mammalian cells has been explored for many years and by a large variety of very different approaches (Schaffer et al., 2008; Lavillette et al., 2001; Soong et al., 2000). Interestingly, however, plant-derived VLPs have not been used for direct gene delivery and expression. In particular, there have been no attempts to use a plant viral capsid to deliver heterologous genes for expression in mammalian cells. High-level expression of mammalian genes in plant hosts, mediated by *Agrobacterium* plasmids containing the translation-enhancement elements from messenger RNAs of the plant virus CPMV, has been demonstrated for various target proteins and vaccines (Sainsbury and Lomonossoff, 2008). The insect virus baculovector system has also been effectively used for expression of mammalian genes in a wide variety of insect and mammalian hosts (Chen et al., 2011), but such a system cannot be reconstituted in vitro and must be prepared by recombinant plasmid engineering in cell culture.

There is a need in the art for new and/or improved virus-like particles that are useful as vectors for the delivery of genes to mammalian cells.

SUMMARY OF THE INVENTION

The present invention provides methods and materials that involve using the capsids of plant viruses as vectors for gene delivery. More particularly, the present invention involves the novel approach of using in vitro reconstituted plant-virus-derived vectors for the packaging and delivery of ribonucleic acid (RNA) genes to mammalian cells. In one aspect of the present invention, a cowpea chlorotic mottle virus (CCMV) capsid protein (CP) is exploited for its unique ability to spontaneously self-assemble around heterologous RNA molecules of widely varying length and sequence. The resulting nucleocapsids—one molecule of RNA surrounded by a rigid single-protein-thick shell—are perfectly monodisperse, stable against aggregation, protect their RNA content against RNases, and release their RNA content in the cytoplasm of target mammalian cells.

Embodiments of the invention include compositions of matter comprising cowpea chlorotic mottle virus capsid proteins and ribonucleic acid. The cowpea chlorotic mottle virus capsid proteins form a capsid that envelops the ribonucleic acid, thereby inhibiting degradation of the ribonucleic acid. Typically in these compositions, the ribonucleic acid encodes a polypeptide, for example a therapeutic polypeptide or a polypeptide that facilitates cellular imaging (e.g. a fluorescent protein). Optionally, the ribonucleic acid encodes a plurality of polypeptides, for example a plurality of therapeutic polypeptides and/or a plurality of polypeptides that facilitate cellular imaging. In some embodiments of the invention, the cowpea chlorotic mottle virus capsid protein is coupled to a polypeptide that binds a molecule expressed on the surface of a mammalian cell (e.g. so as to facilitate targeting of a specific cellular lineage).

Another embodiment of the invention is a method of making a ribonucleic acid packaged within a cowpea chlorotic mottle virus capsid, the method comprising combining cowpea chlorotic mottle virus capsid protein and a ribonucleic acid in a solution in vitro so as to form a composition as disclosed herein. In these methods, relative amounts of cowpea chlorotic mottle virus capsid protein and ribonucleic acid that are combined are controlled so as to control packaging of the ribonucleic acid in the cowpea chlorotic mottle virus capsid. For example, in some embodiments of the invention, relative amounts of cowpea chlorotic mottle virus capsid protein and ribonucleic acid are controlled so that there are at least 10 cowpea chlorotic mottle virus capsid proteins for every 100 nucleotides of ribonucleic acid molecule length (e.g. 150 capsid proteins for a 1,500 nt ribonucleotide). In some embodiments of the invention, relative amounts of cowpea chlorotic mottle virus capsid protein and ribonucleic acid are controlled so that the mass ratio of cowpea chlorotic mottle virus capsid proteins to ribonucleic acids is at least 6:1.

Yet another embodiment of the invention is a method of delivering a ribonucleic acid into the cytoplasm of a mammalian cell, the method comprising combining the mammalian cell with a composition comprising a ribonucleic acid enveloped by a cowpea chlorotic mottle virus capsid, and then allowing the cowpea chlorotic mottle virus capsid to contact the mammalian cell and deliver the ribonucleic acid into the cytoplasm of a mammalian cell (e.g. a mammalian cancer cell, a mammalian cell of a selected lineage or the like). Typically in these methods, the ribonucleic acid is at least 100 nucleotides in length and is not derived from a cowpea chlorotic mottle virus or other virus. Typically, the ribonucleic acid encodes at least one polypeptide that is expressed in the mammalian cell following delivery of the ribonucleic acid into the cytoplasm of the mammalian cell. In one illustrative embodiment of the invention, the ribonucleic acid encodes a mammalian (e.g. human) polypeptide, for example a polypeptide useful in a therapeutic regimen. In another illustrative embodiment of the invention, the ribonucleic acid encodes a polypeptide selected for its ability to facilitate imaging of the mammalian cell.

Other objects, features and advantages of the present invention will become apparent to those skilled in the art from the following detailed description. It is to be understood, however, that the detailed description and specific examples, while indicating some embodiments of the present invention are given by way of illustration and not limitation. Many changes and modifications within the scope of the present invention may be made without departing from the spirit thereof, and the invention includes all such modifications.

BRIEF DESCRIPTION OF THE DRAWINGS

FIG. 9 provides a diagram illustrating that electrostatic interactions are dominant in driving virus and VLP assembly. All lengths and sequences of RNA, from 100 nt to 10,000 nt can be completely packaged by CCMV capsid protein CP, if the CP:RNA mass ratio is high enough. This threshold mass ratio (6:1) is the same for all RNA lengths, corresponding to approximately 10 CP per 100 nt (+10 charges/CP N-terminus; −1 charge/nt). I.e., this ("magic") ratio involves matching the RNA charge with the N-terminal capsid protein (CP) charge.

FIG. 14 is a transmission electron microscopy (TEM) image of CCMV capsids (containing the DNA oligo agonist for Herpes vaccine) wrapped by a neutral/cationic lipid membrane. This image shows that in vitro-reconstituted CCMV VLPs can be wrapped in vitro by bilayer membrane, to make enveloped virus-like particles (EVLPs) for gene and vaccine delivery.

DETAILED DESCRIPTION OF THE INVENTION

Figure 1:
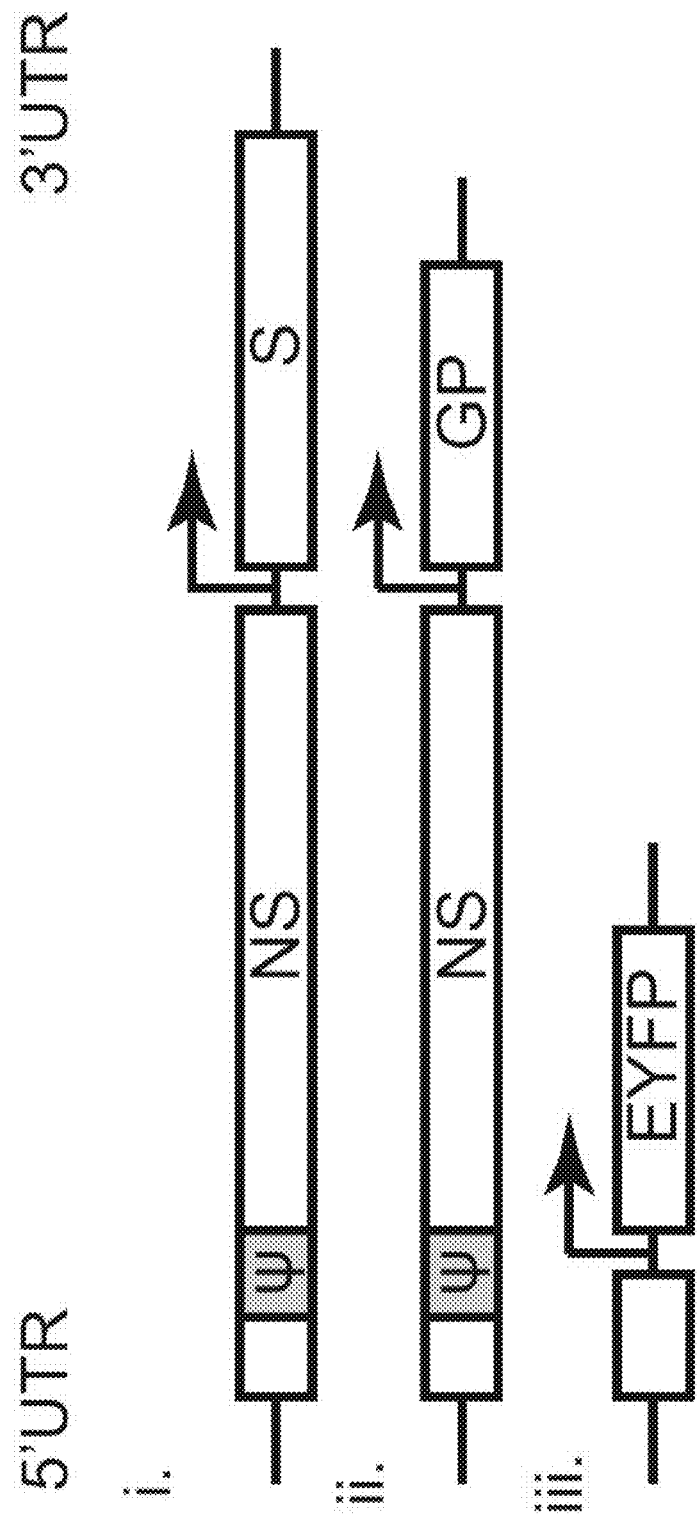
FIG. 1 illustrates schematics of the relevant RNA reagents. (i) Wt SINV genome. The blocks labeled NS and S are the open reading frames coding for the replicase proteins and the structural proteins ([CP] and [GPs]). Ψ denotes the packaging signal, a sub-sequence in NS responsible for the preferential packaging of the RNA by its capsid protein. The hook-arrow denotes the promoter sequence controlling transcription of the downstream (structural, S) genes. (ii) GP-replicon RNA. Same as i, except for deletion of the CP gene. (iii) DI[EYFP] RNA. Derived from I upon deletion of most of the NS ORF and replacement of the structural genes (S ORF) with EYFP ORF. The Ψ signal is not present, but the cis-acting elements—the 5' and 3' untranslated regions (UTRs) needed for replication by the NS complex—are retained.

Unless otherwise defined, all terms of art, notations and other scientific terms or terminology used herein are intended to have the meanings commonly understood by those of skill in the art to which this invention pertains. Many of the techniques and procedures described or referenced herein are well understood and commonly employed using conventional methodology by those skilled in the art. It is to be understood that other embodiments may be utilized and structural changes may be made without departing from the scope of the present invention.

For example, many of the pertinent techniques and methodologies described or referenced herein with regards to the present invention are readily available in the literature. These include: genetic engineering protocols for point-site mutation of capsid protein (e.g., to insert cysteines on the capsid exterior for ligand binding) and for fusions of it with polypeptide domains desirable for targeting and uptake by specific cells; molecular biology techniques (e.g., *agrobacterium* transfer of mutated capsid protein genes to host plants) for scaling up the synthesis of capsid protein for self-assembly reactions with RNA genes and gene of interest (GOI)-containing RNA replicons; and mouse models for in vivo testing of the in vitro reconstituted vectors described herein (e.g., of the delivery of ferritin genes and their expression in targeted cell tissue for MRI molecular imaging).

The present invention involves the use of plant viral capsids as vectors for gene delivery. More particularly, the present invention involves the use of in vitro reconstituted plant-virus-derived vectors for the packaging and delivery of ribonucleic acid (RNA) genes into mammalian cells. Generally, such plant virus capsids—synthesized from purified components—contain replicon RNA with a gene of interest that is expressed at a high copy number when the capsid is delivered to the cytoplasm of mammalian cells.

DNA and RNA viruses have qualitatively different life cycles due to the fact that their genomes (double-stranded DNA and single-stranded RNA) are fundamentally different physical objects. More explicitly, the former (DNA) is a stiff, linear, polymer, while the latter (RNA) is a flexible, branched polymer. As a consequence, for example, DNA viruses are strongly pressurized, requiring for their formation considerable expenditure of energy, while RNA viruses can self-assemble spontaneously, resulting in their infectivities being associated with very different mechanisms of genome packaging and delivery.

In one aspect of the present invention, cowpea chlorotic mottle virus (CCMV) capsid protein (CP) is exploited for its unique ability to spontaneously self-assemble around heterologous RNA molecules of widely varying length and sequence. CCMV is a spherical virus that can be reconstituted 'from scratch', i.e., synthesized "in vitro" from its purified components, namely the viral RNA genome and capsid protein. Furthermore, the capsid protein will package, via spontaneous self-assembly, not only its viral genome, but also all kinds of other RNA molecules. The resulting virus-like particles are stable against aggregation and their protein shells protect their RNA cargo against nuclease (RNase) enzymes. Processes for manipulating CCMV capsid proteins are known in the art and described, for example, in U.S. Pat. Nos. 6,180,389, 7,928,290, and United States Patent Application Publication Nos. 20090093019 and 20120174263, the contents of which are incorporated by reference.

Unlike mammalian viruses—the majority of whose nucleocapsids are enveloped by an extra layer of protection in the form of a viral envelope—plant viruses are almost without exception "just" genetic material (DNA or RNA) surrounded by a shell composed of the capsid protein (CP). Because the viral genome is protected only by this protein shell, the resulting nucleocapsid (nucleic acid packaged inside a capsid) is significantly more robust than its counterpart in enveloped animal viruses. The nucleocapsids disclosed herein are perfectly monodisperse (in one example, 26 nm in diameter), stable against aggregation, protect their RNA content against RNases, and release their RNA content in the cytoplasm of target mammalian cells.

Further, an RNA gene of interest (GOI) packaged in accordance with the present invention can be expressed in mammalian cells following replication by RNA-dependent RNA polymerases (RDRPs) provided in trans. If the packaged molecule is a replicon containing a GOI, the RNA may be replicated up to one-million-fold (by the RDRP enzymes for which it encodes) before the GOI is translated and its protein product synthesized in high copy number. In one or more embodiments, the replicon and target gene may be separated into two molecules and each packaged separately into single capsids.

A variety of replicons that can be adapted for use with embodiments of the invention are known in the art (see, e.g. U.S. Pat. Nos. 6,462,255 and 7,807,868 and U.S. Patent Publication Nos. 20030119182, 20080282426 and 20060253939, the contents of which are incorporated by reference herein). In one or more embodiments, a replicon from a Nodamura virus is used. The replicon is short enough to be packaged in a single capsid, even when a reporter gene is added to it. The capsid protein provided can package into a single protective shell any RNA with lengths between 2000 and 4000 nucleotides, without it needing to be genetically engineered with a "packaging signal". Moreover, there are a wide variety of methods for functionalization to various icosahedral capsids, allowing them to be targeted to specific cells.

In embodiments of the invention, a composition of matter is provided comprising a cowpea chlorotic mottle virus capsid protein (CCMV CP) and a ribonucleic acid (RNA). The ribonucleic acid is not derived from a cowpea chlorotic mottle virus and the cowpea chlorotic mottle virus capsid protein envelops the ribonucleic acid so as to inhibit degradation of the ribonucleic acid. In one or more embodiments, the ribonucleic acid does not need to be engineered with a packaging signal and/or an origin of assembly. A packaging signal or origin of assembly is commonly used for the preferential packaging of ribonucleic acid by a capsid protein. See, e.g. Smith et al., 2007 and Mahraj et al., 2014, which describe Tobacco Mosaic virus (TMV) coat protein (CP) reassembly onto RNA that requires a TMV origin-of-assembly (OA) (see, e.g. SEQ ID NO: 2). The ability to package any RNA at all, without needing it to be genetically engineered with a packaging signal or origin of assembly, is a major advantage that eliminates the complexities, costs, and increased size associated with incorporating a packaging signal or origin of assembly into a replicon or RNA.

Embodiments of the invention include compositions of matter comprising cowpea chlorotic mottle virus capsid proteins and ribonucleic acid. In these compositions, the ribonucleic acid is at least 100 nucleotides in length and is not derived from a cowpea chlorotic mottle virus. The cowpea chlorotic mottle virus capsid proteins form a capsid that envelops the ribonucleic acid, thereby inhibiting degradation of the ribonucleic acid. In certain embodiments of the invention the composition further comprises a mammalian cell. Typically in these compositions, the ribonucleic acid encodes a polypeptide, for example a therapeutic polypeptide or a polypeptide that facilitates cellular imaging (e.g. a iron-sequestering ferritin protein, a green fluorescent protein or the like). Optionally, the ribonucleic acid encodes a plurality of polypeptides, for example a plurality of therapeutic polypeptides and/or a plurality of polypeptides that facilitate cellular imaging. In an illustrative embodiment, the ribonucleic acid encodes a plurality of polypeptides including a RNA-dependent RNA polymerase. In some embodiments of the invention, the cowpea chlorotic mottle virus capsid protein is coupled to a polypeptide binds a molecule expressed on the surface of a mammalian cell (e.g. so as to facilitate targeting of a specific cellular lineage, a cancer cell or the like).

Figure 10:
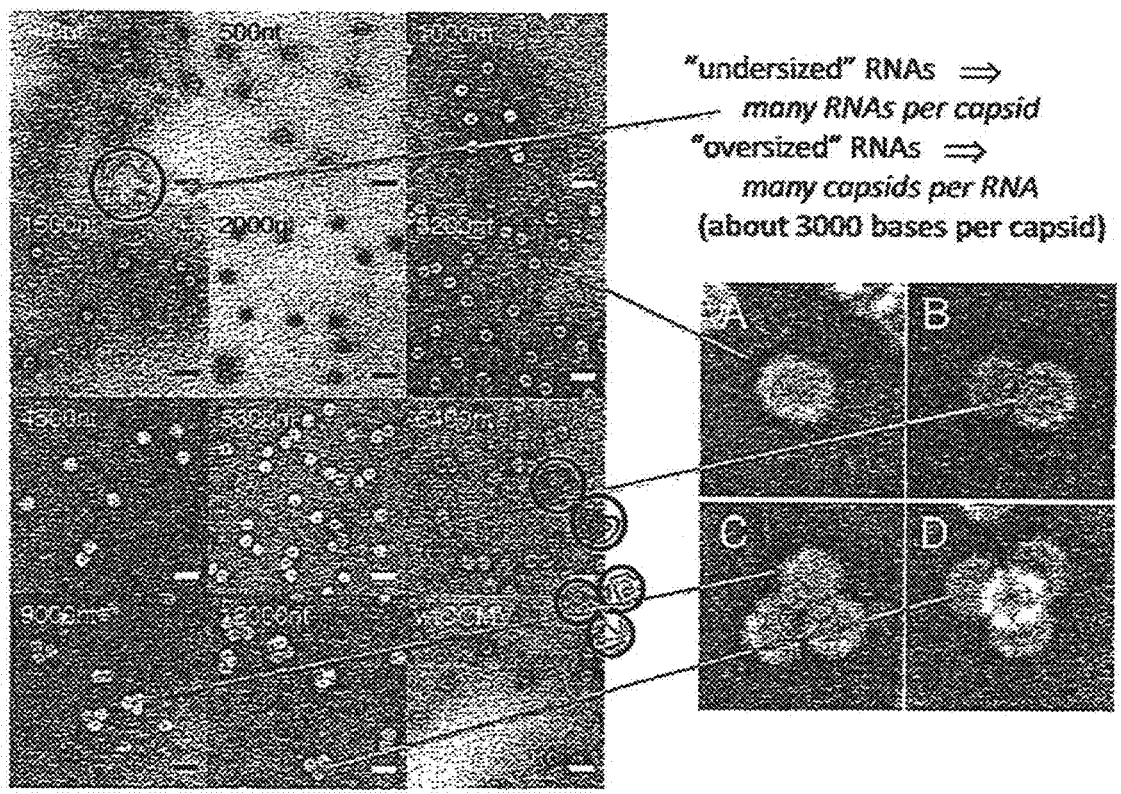
FIG. 10 is a collection of images illustrating that CCMV protein can self-assemble with RNAs of many lengths. "Undersized" RNAs (less than 2000 nts) lead to many RNAs per capsid. "Oversized" RNAs (more than 4000 nts) lead to many capsids per RNA (about 3000 bases per capsid).
Figure 11:
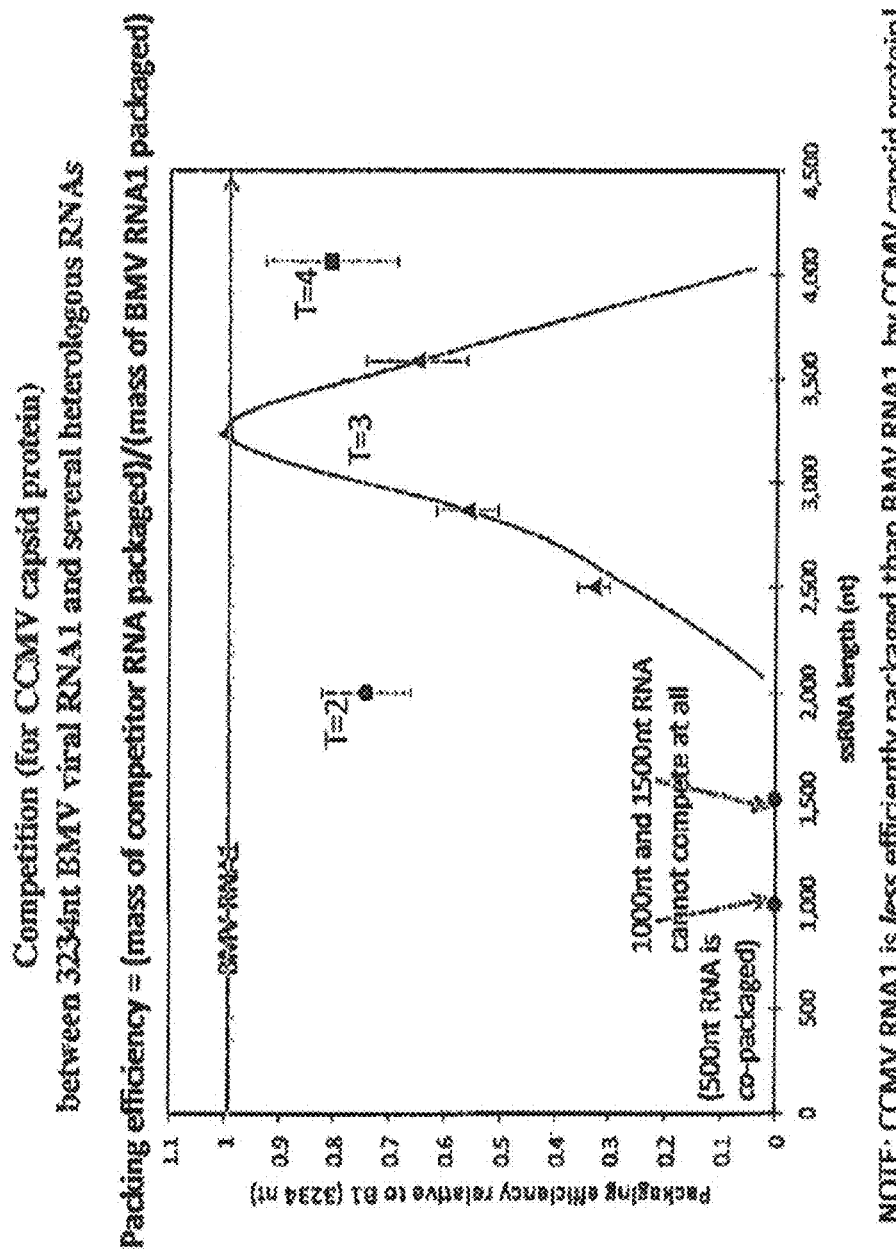
FIG. 11 is a graph illustrating the competition (for CCMV capsid protein) between 3234 nt BMV viral NRA1 and several heterologous NRAs. Packing efficiency=(mass of competitor RNA packaged)/(mass of BMV RNA1 packaged). 500 nt RNA is co-packaged. 1000 nt and 1500 nt RNA cannot compete at all. Note that CCMV RNA1 is less efficiently packaged than BMV RNA1 by CCMV capsid protein.
Figure 12:
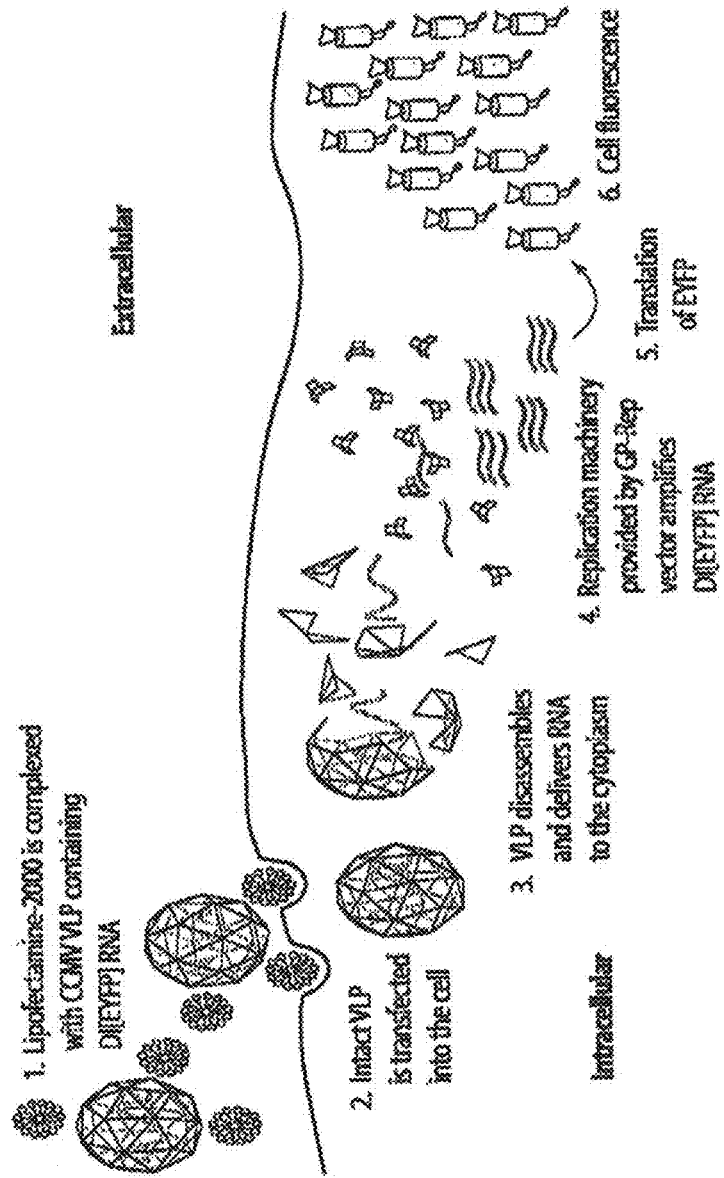
FIG. 12 is a diagram illustrating a process in which plant (CCMV) capsids release mRNA for expression in mammalian (BHK) cells. This takes advantage of the robustness of CCMV nucleocapsids and of the promiscuity of their capsid protein. Plant (CCMV) capsids can release mRNA for expression in mammalian (BHK) cells. In a first step, lipofectamine-2000 is complexed with CCMV VLP containing DI[EYFP] RNA. In a second step, intact VLP is transfected into the cell. In a third step, VLP disassembles and delivers RNA to the cytoplasm. In a fourth step, replication machinery provided by GP-Rep vector amplifies DI[EYFP] RNA. In a fifth step, translation of EYFP occurs. In a sixth step, cell fluorescence results.
Figure 13:
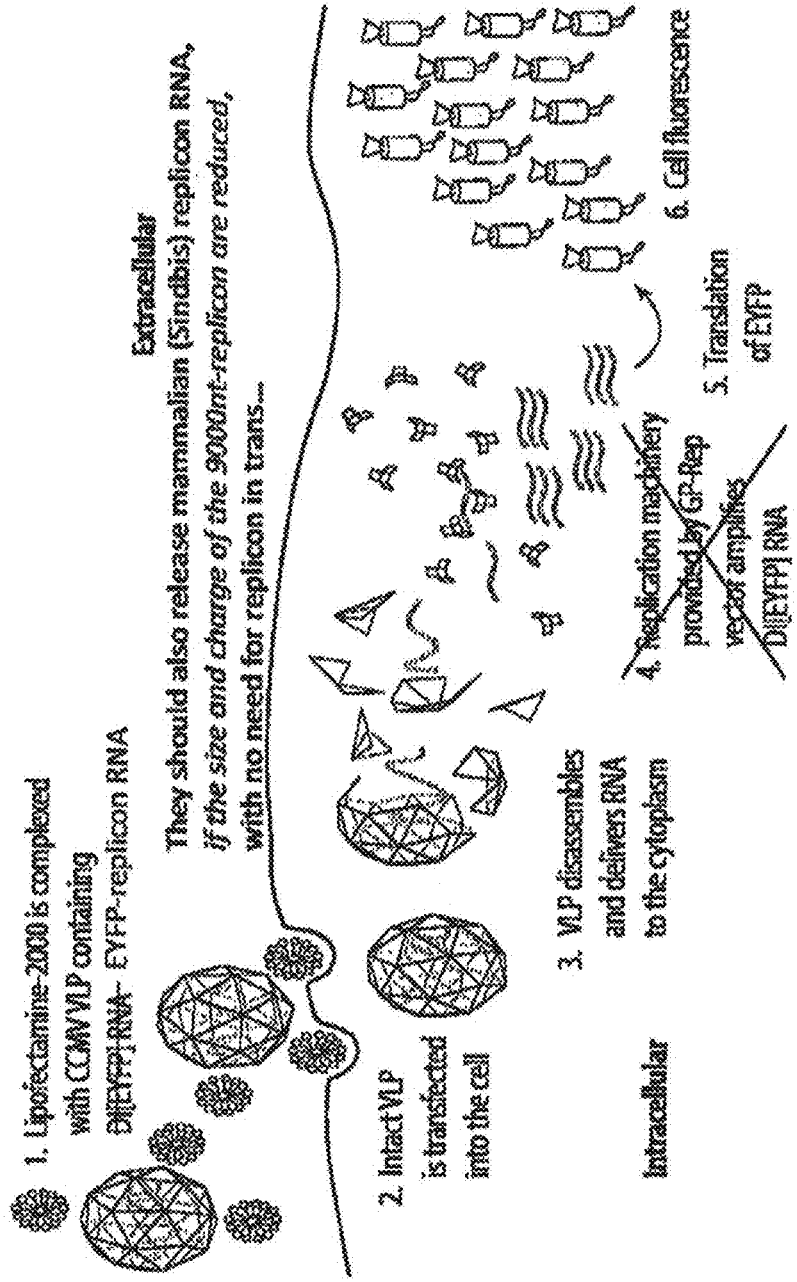
FIG. 13 is a diagram illustrating another process in which plant (CCMV) capsids release mRNA for expression in mammalian (BHK) cells. In a first step, lipofectamine-2000 is complexed with CCMV VLP containing EYFP-replicon RNA. They should also release mammalian (Sindbis) replicon RNA, if the size and charge of the 9000 nt-replicon are reduced, with no need for replicon in trans. In a second step, intact VLP is transfected into the cell. In a third step, VLP disassembles and delivers RNA to the cytoplasm. Translation of EYFP occurs and then cell fluorescence results.

In typical embodiments of the invention, the ribonucleic acid in the composition is between 100 and 10,000 nucleotides in length; and/or comprises at least 1,000 nucleotides, at least 2,000 nucleotides, at least 3,000 nucleotides, at least 4,000 nucleotides, or at least 5,000 nucleotides; and/or does not include a signal sequence that modulates packaging of the ribonucleic acid by the capsid proteins (e.g. a viral origin-of-assembly element). Typically, the capsid envelopes a single ribonucleic acid molecule. In certain embodiments of the invention, the relative amounts of cowpea chlorotic mottle virus capsid protein and ribonucleic acid that are combined together are selectively controlled to form a composition wherein there are at least 10 cowpea chlorotic mottle virus capsid proteins for every 100 nucleotides of ribonucleic acid length. In some embodiments of the invention, the relative amounts of cowpea chlorotic mottle virus capsid protein and ribonucleic acid that are combined together are controlled to form a composition wherein the mass ratio of cowpea chlorotic mottle virus capsid proteins to ribonucleic acids is at least 6:1. As shown by the data presented in FIGS. 9-11, by controlling the relative amounts of cowpea chlorotic mottle virus capsid protein and ribonucleic acid in this manner, the packaging of selected ribonucleic acids can be controlled.

Optionally, the cowpea chlorotic mottle virus capsid protein is coupled to a polypeptide that is not derived from a cowpea chlorotic mottle virus, for example a polypeptide that binds a molecule expressed on the surface of a mammalian cell (e.g. a cowpea chlorotic mottle virus capsid protein coupled to a polypeptide comprising an antibody epitope that can bind a cellular protein on the surface of the mammalian cell). In one or more embodiments, the ribonucleic acid does not include a "packaging signal" used for the preferential packaging of ribonucleic acid by a capsid protein. In one illustrative embodiments, the packaging signal comprises AAGAAGUCG of SEQ ID NO: 2.

Another embodiment of the invention is a method of making a ribonucleic acid packaged within a cowpea chlorotic mottle virus capsid, the method comprising combining cowpea chlorotic mottle virus capsid protein and a ribonucleic acid in a first buffer solution in vitro so as to form a composition as disclosed herein. In these methods, relative amounts of cowpea chlorotic mottle virus capsid protein and ribonucleic acid that are combined are controlled so as to control packaging of the ribonucleic acid in the cowpea chlorotic mottle virus capsid. For example, in some embodiments of the invention, relative amounts of cowpea chlorotic mottle virus capsid protein and ribonucleic acid are controlled so that there are at least 10 cowpea chlorotic mottle virus capsid proteins for every 100 nucleotides of ribonucleic acid molecule length. In some embodiments of the invention, relative amounts of cowpea chlorotic mottle virus capsid protein and ribonucleic acid are controlled so that the mass ratio of cowpea chlorotic mottle virus capsid proteins to ribonucleic acids is at least 6:1. Optionally, the method further comprises coupling the cowpea chlorotic mottle virus capsid with a membrane comprising a lipid, for example a bilayered membrane that envelops the cowpea chlorotic mottle virus capsid.

The methods can further comprise dialyzing the first buffer solution against a second buffer solution; and/or treating the capsid with a ribonuclease. For example, the methods can comprise the steps of incubating the cowpea chlorotic mottle virus capsid protein and the ribonucleic acid together in a solution having a neutral pH and then dialyzing the incubated mixture of step (a) within a buffer solution. In typical embodiments the first buffer solution has a neutral pH (e.g. a pH between 7.0 and 7.4), and the second buffer solution has a pH below 5.0. In one illustrative embodiment of the invention, one can mix capsid protein and RNA (ranging in length from 100 nt to 10,000 nt) in pH 7.2 (I=0.1M) buffer, incubate the mixture overnight, and then dialyze against pH 4.8 (I=0.1M) buffer. In these methods, one can treat assemblies with RNase to remove unpackaged RNA. One can then analyze the particles by gel electrophoresis, sucrose gradients, and electron microscopies (and/or by packaging fluorescently labeled RNAs etc.). In addition, as disclosed herein, the relative amounts or ratios of combined RNAs and capsid proteins can be controlled to allow "Head-to-Head" packaging competition experiments. By doing this, one can mix equal masses of two RNAs of different lengths with sufficient protein to completely package only one of them (see, e.g. the data presented in FIG. 11).

Yet another embodiment of the invention is a method of delivering a ribonucleic acid into the cytoplasm of a mammalian cell, the method comprising combining the mammalian cell with a composition comprising a ribonucleic acid enveloped by a cowpea chlorotic mottle virus capsid, and then allowing the cowpea chlorotic mottle virus capsid to contact the mammalian cell and deliver the ribonucleic acid into the cytoplasm of a mammalian cell (e.g. a mammalian cancer cell, a mammalian cell of a selected lineage or the like). Typically in these methods, the ribonucleic acid is at least 100 nucleotides in length and is not derived from a cowpea chlorotic mottle virus or other virus. Typically, the ribonucleic acid encodes at least one polypeptide that is expressed in the mammalian cell following delivery of the ribonucleic acid into the cytoplasm of the mammalian cell. In one illustrative embodiment of the invention, the ribonucleic acid encodes a mammalian (e.g. human) polypeptide, for example a polypeptide useful in a therapeutic regimen. In another illustrative embodiment of the invention, the ribonucleic acid encodes a polypeptide selected for its ability to facilitate imaging of the mammalian cell. In certain embodiments of the invention, the ribonucleic acid encodes a RNA-dependent RNA polymerase.

In other embodiments of the invention, a method of delivering a ribonucleic acid into the cytoplasm of a mammalian cell is provided. The method comprises the steps of combining the mammalian cell with the composition of matter described herein under conditions selected to allow the cowpea chlorotic mottle virus capsid protein to contact the mammalian cell and deliver the ribonucleic acid into the cytoplasm of a mammalian cell. In various embodiments, the ribonucleic acid encodes at least one polypeptide that is expressed in the mammalian cell following delivery of the ribonucleic acid into the cytoplasm of the mammalian cell.

As illustrated in the Example section below, the in vitro reconstituted virus-like particles disclosed herein—whose protein shells are made of plant viral, Cowpea Chlorotic Mottle Virus (CCMV), capsid protein—are capable of releasing their RNA cargo in mammalian cells. In the illustrative example, hybrid virus-like particles, assembled in vitro from Cowpea Chlorotic Mottle Virus (CCMV) capsid protein (CP) and a heterologous RNA derived from a mammalian virus (Sindbis), were shown to be capable of releasing their RNA in the cytoplasm of mammalian cells. Moreover, the reporter genes included in the RNA were expressed, resulting in a high level of protein synthesis.

In another aspect of the present invention, the cytoplasmic entry of the RNA-containing nucleocapsid can be facilitated by conjugating the CCMV capsid protein with a ligand that binds to target cells and induces endocytosis. Important examples include the targeted delivery of vaccines in RNA form, MRI contrast agents (e.g., iron-sequestering ferritin protein) in RNA form, and a variety of therapeutic proteins (e.g., super oxide dismutase (SOD)) in RNA form.

Work by many others in the art has shown that the outside of the protein shells of plant viruses like CCMV can be chemically modified so that they target and are taken up by specific mammalian cells. Thus, chemical and biological techniques may be used for mutating the CCMV capsid protein so that the exterior surface of the nucleocapsid is functionalized for targeting and uptake by specific cells. For example, if the capsid protein ligand involved is an antibody to a specific cancer-cell-presenting antigen, and the GOI codes for ferritin, one is able to test directly in mouse models the efficacy of MRI to produce contrast enhancement in cells due to the vector.

In another embodiment of the invention, a method of making the composition of matter described above is provided. The method comprises combining the cowpea chlorotic mottle virus capsid protein and the ribonucleic acid in a solution in vitro. The method further comprises the steps of (a) incubating the cowpea chlorotic mottle virus capsid protein and the ribonucleic acid together in a solution having a neutral pH and (b) dialyzing the incubated mixture of step (a) within a buffer solution.

In other embodiments of the invention, a method of delivering a ribonucleic acid into the cytoplasm of a mammalian cell is provided. The method comprises the steps of combining the mammalian cell with the composition of matter described herein under conditions selected to allow the cowpea chlorotic mottle virus capsid protein contact the mammalian cell and deliver the ribonucleic acid into the cytoplasm of a mammalian cell. In various embodiments, the ribonucleic acid encodes at least one polypeptide that is expressed in the mammalian cell following delivery of the ribonucleic acid into the cytoplasm of the mammalian cell.

In certain instances, the method comprises intravenous injection of aqueous solutions of the RNA-containing functionalized nucleocapsids disclosed herein. Experimental animal models, such as mouse models, may be used to further test and optimize the efficacy of the methods for delivering, in separate experiments, the following proteins: influenza vaccines, ferritin for MRI contrast, and superoxide dismutase.

One unique aspect—and a distinct advantage—of the present invention is the delivery of genes to mammalian cells within the capsid of a self-assembling plant virus rather than packaging them in a mammalian virus or in liposomes. The in vitro assembly from purified components avoids the use of cell cultures and provides monodisperse, well-defined, and robust particles that are functionalized for targeting of and uptake by mammalian cells.

The present invention is also significant in that, for example, instead of trying to deliver desired proteins (e.g., vaccines or enzymes or toxins) to specific cells, it is more powerful to deliver the RNA genes for these proteins to the cells. By packaging a GOI-containing replicon, the present invention can be used to deliver—not a single protein, but rather—a self-amplifying RNA gene for that protein, thereby ensuring a high level of expression. Accordingly, the present invention allows for the usage of well-characterized, stable, long-shelf-life, in vitro synthesized, virus-like particles to deliver RNA genes to targeted cells.

The Example section below illustrates packaging an RNA gene of interest in virus-like particles, getting the particle into mammalian cells, and providing in trans an RNA replicon molecule that replicates the RNA gene a million-fold before the gene is translated into protein. However, in certain embodiments the RNA gene and the replicon may be packaged as a single RNA molecule, so that the resulting virus-like particle is capable—all by itself—of protecting, delivering, amplifying, and expressing the target gene in specific mammalian cells. In one illustrative example, a single RNA molecule with two open reading frames—one containing the RDRP genes of Nodamura virus and the other the EYFP GOI—is packaged by a CCMV capsid protein. Transfection of these reconstituted nucleocapsids result directly in EFYP expression. In other embodiments, the replicon and target gene are packaged separately into single capsids.

EXAMPLE

Reconstituted Plant Viral Capsids can Release Genes to Mammalian Cells

This example illustrates in vitro packaging by CCMV capsid protein of an RNA gene coding for a fluorescent protein, EYFP (see also, Azizgolshani, et al. Virology 441 (2013) 12-17). The resulting nucleocapsids are delivered by transfection to mammalian (baby hamster kidney [BHK]) cells, with RDRPs provided in trans, and EYFP expression (fluorescence) observed directly.

The nucleocapsids of many plant viruses are significantly more robust and protective of their RNA contents than those of enveloped animal viruses. In particular, the capsid protein (CP) of the plant virus Cowpea Chlorotic Mottle Virus (CCMV) is of special interest because it has been shown to spontaneously package, with high efficiency, a large range of lengths and sequences of single-stranded RNA molecules. This example demonstrates that hybrid virus-like particles, assembled in vitro from CCMV CP and a heterologous RNA derived from a mammalian virus (e.g. Nodamura, Sindbis), are capable of releasing their RNA in the cytoplasm of mammalian cells. This result demonstrates the use of plant viral capsids as vectors for gene delivery and expression in mammalian cells. Furthermore, the CCMV capsid protects the packaged RNA against nuclease degradation and serves as a robust external scaffold with many possibilities for further functionalization and cell targeting.

The use of animal virus-like particles (VLPs) as vectors for the delivery of genes to mammalian cells has been explored for many years and by a large variety of very different approaches (Schaffer et al., 2008; Lavillette et al., 2001; Soong et al., 2000). This example examines the possibility of using a well-characterized plant RNA virus for expression of heterologous genes in mammalian cells. Unlike mammalian viruses—the majority of whose nucleocapsids are enveloped by an extra layer of protection in the form of a viral envelope—plant viruses are almost without exception "just" genetic material (DNA or RNA) surrounded by a shell composed of the capsid protein (CP). Because the viral genome is protected only by this protein shell, the resulting nucleocapsid (nucleic acid packaged inside a capsid) is significantly more robust than its counterpart in enveloped animal viruses.

Consider, for example, the "superfamily" of single-stranded RNA viruses comprised of bromoviruses (infecting plants) and alphaviruses (infecting animals), and whose members include Cowpea Chlorotic Mottle Virus (CCMV) and Sindbis Virus (SINV), respectively (Strauss and Strauss, 1994). The nucleocapsids of both CCMV (Bancroft and Hiebert, 1967; Zhao et al., 1995; Fox et al., 1998) and SINV (Wengler et al., 1982; Tellinghuisen et al., 1999; Mukhopadhyay et al., 2002; Giocochea et al., 2007; Cheng and Mukhopadhyay, 2011) have been reconstituted in vitro from purified components. However, the nucleocapsids of CCMV are much more stable in solution than those of SINV. Furthermore, in contrast to STNV nucleocapsids that have evolved to depend on their viral envelope for protection against nucleases, CCMV capsids protect their RNA content against digestion.

Equally important, CCMV capsid protein has been shown to be capable of packaging, via spontaneous in vitro self-assembly, a wide range of non-viral cargo, including: heterologous RNAs (Hiebert et al., 1968; Bancroft et al., 1969; Rao, 2006), synthetic anionic polymers (Douglas and Young, 1998; Hu et al., 2008; Brasch and Cornelissen, 2012; Cadena-Nava et al., 2011), mineralized salts (Douglas andYoung, 1998), negatively charged colloidal particles such as gold nanoparticles (Chen et al., 2006) and oil-in-water nanoemulsion droplets (Chang et al., 2008), fluorescent proteins (Minten et al., 2009), and pH-controlled chromophores (Brasch et al., 2011). In addition, by functionalizing and chemically modifying their capsids, closely-related plant viruses like Cowpea Mosaic Virus (CPMV) have been used for targeting of and uptake by specific mammalian cells for imaging and drug delivery (Destito et al., 2007; Gonzales et al., 2009; Yildiz et al., 2011; Steinmetz, 2010; Wu et al., 2012). Similarly, MS2 VLPs containing a variety of drugs, siRNAs, and toxins have been conjugated with peptide ligands and shown to produce selective cytotoxicity in cancer cells (Ashley et al., 2011).

Plant-derived VLPs, however, have not been used for direct gene delivery and expression, although a recent study (Li et al., 2012) reports the transfection of tobacco mosaic virus (TMV) virions into HeLa cells with the resulting expression of TMV capsid protein; see also the 2007 *Virology* and 2014 *Int. J. Mol. Sci.* papers of McCormick and co-workers. Interestingly, high-level expression of mammalian genes in plant hosts, mediated by *Agrobacterium* plasmids containing the translation-enhancement elements from messenger RNAs of the plant virus CPMV, has been demonstrated for various target proteins and vaccines (Sainsbury and Lomonossoff, 2008). The insect virus baculovector system has also been effectively used for expression of mammalian genes in a wide variety of insect and mammalian hosts (Chen et al., 2011), but unlike the system we describe here it cannot be reconstituted in vitro and must be prepared by recombinant plasmid engineering in cell culture.

There have been no attempts to use a spherical plant viral capsid to deliver heterologous genes for expression in mammalian cells, even though there are several independent demonstrations of the internalization of plant virus by such cells. Examples include the membrane-protein-mediated uptake of CPMV by mouse vascular endothelial cells (Koudelka et al., 2009) and the uptake of brome mosaic virus (BMV) by human bronchial epithelial cells (Jung et al., 2011).

The possibility of uptake and release of the contents of a plant capsid in a mammalian cell has been suggested in the case of red clover necrotic mosaic virus (RCNMV) (Lockney et al., 2011). In particular, capsids of purified virus loaded with doxorubicin were functionalized with HeLa cell-targeting peptides, and the survivability of HeLa cells overlaid by them shown to decrease with doxorubicin concentration. While disassembly of the capsids in the HeLa cells was not directly established, doxorubicin was argued to be released by the same divalent cation-controlled mechanism as known to occur with RCNMV RNA in plant cell hosts.

In light of there being no direct demonstration of spherical plant viruses disassembling and thereby releasing their contents in animal cells, the question considered is whether heterologous genes in spherical plant VLPs can be made available to a mammalian cell and their protein products synthesized?

In answering this question, and thereby providing a new platform for gene delivery to mammalian cells, many unique in vitro reconstitution properties of the spherical plant virus, CCMV is exploited. In particular—in contradistinction to the CPMV and RCNMV examples mentioned above—the purified capsid protein of CCMV is capable of efficiently packaging a large range of RNA lengths and sequences, including arbitrary transgenes of interest. If these in vitro synthesized VLPs can be shown to disassemble and release their RNA contents in mammalian cells, then the stage is set for functionalizing the capsids to target those cells in vivo.

The strategy is as follows: A well-characterized VLP consisting of a reporter ssRNA molecule packaged inside a CCMV capsid is reconstituted in vitro. To this end, a SINV-derived defective interfering RNA (DI[EYFP], 1800 nt: FIG. 1iii) is designed, which upon transcription produces the mRNA for expression of high levels of enhanced yellow fluorescent protein (EYFP). The VLPs containing DI[EYFP] are transfected into a monolayer of baby hamster kidney (BHK) cells. The machinery for the transcription and replication of the DI[EYFP] RNA is supplied by a SINV-like particle (GP-Rep vector: FIG. 1ii) providing the replicase proteins that will efficiently replicate the DI[EYFP] RNA molecule if and only if the encapsidated DI[EYFP] RNA is released from the VLPs upon internalization. Therefore, the expression of EYFP in vector-infected, VLP-transfected, cells can report on the successful release of the encapsidated RNA for transcription, replication and translation.

FIG. 1 shows schematically the coding and regulatory sequences of the full SINV RNA genome (i), highlighting the two open reading frames (ORFs) coding for the non-structural (NS) genes (RNA-dependent RNA polymerase) and structural (S) genes (capsid protein (CP) and membrane glycoproteins (GP)). Also shown is the SINV-derived glycoprotein "replicon" (GP-Rep) RNA (ii), obtained by deleting the CP gene in the full SINV genome (see Methods section). A defective-interfering (DI) RNA molecule (iii) is derived from it by deleting most of the nonstructural ORF and replacing the structural genes by the EYFP gene (see Methods section).

Results and Discussion

VLP Synthesis and Characterization

As described in the Methods section below, DI[EYFP] RNA and an excess of CCMV CP are subjected to the standard protocol for in vitro reconstitutions of RNA and CCMV CP. Basically, they are incubated together at neutral pH and then dialyzed against pH 4.8 buffer solution.

Figure 2:
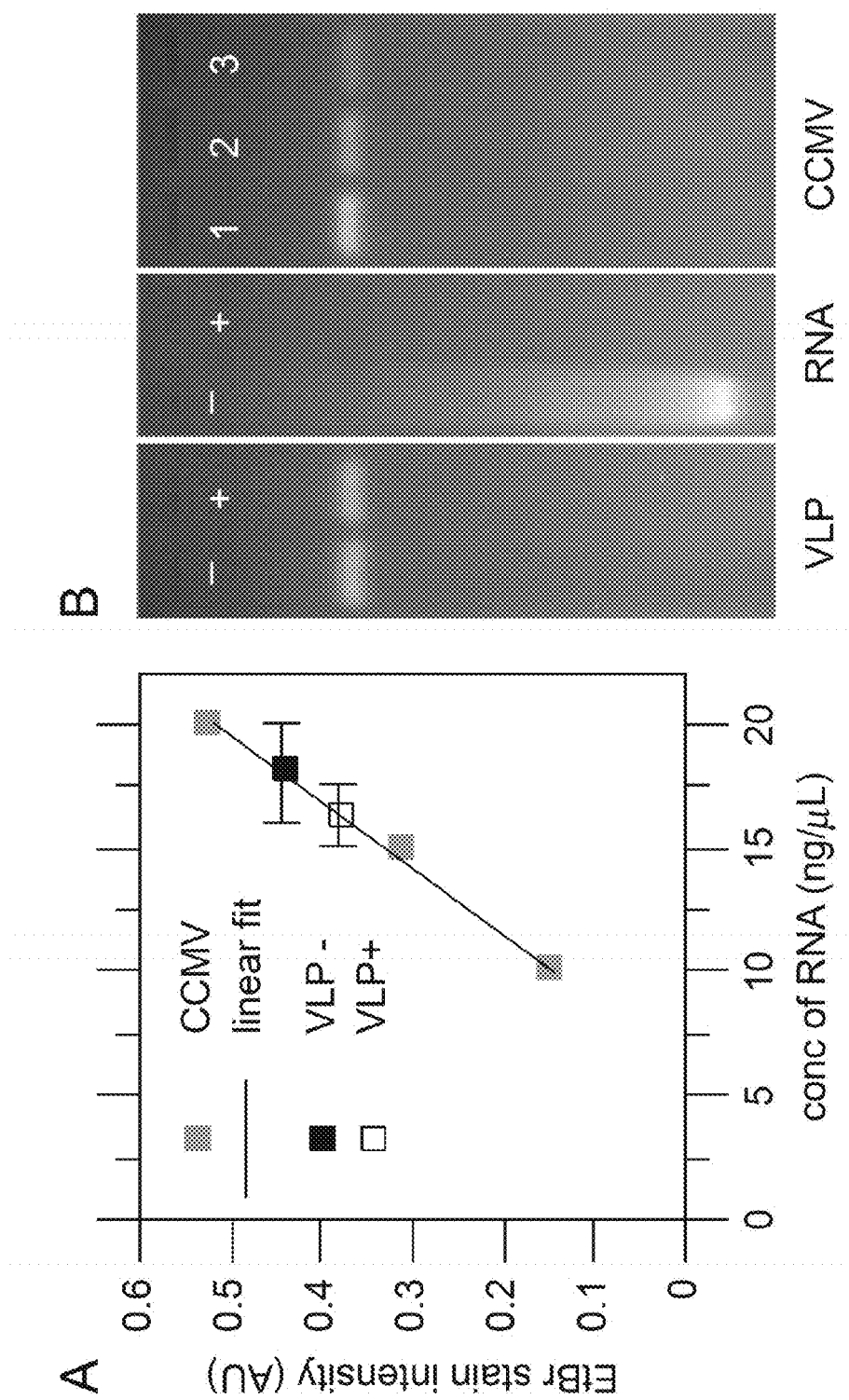
FIG. 2 illustrates (A) Quantification of VLPs by densitometry. The densitometry plot quantifies the amount of RNA packaged in VLPs by measuring the EtBr fluorescence intensity from CCMV bands of known concentration. (B) Agarose gel electrophoresis of synthesized VLPs, naked DI[EYFP] 1800 nt-RNA, and CCMV particle standards with known concentrations. Electrophoresis was carried out in a 1% agarose gel and in virus buffer (VB: see Methods section); the gel was stained with EtBr. (+) and (−) designations refer to the presence or absence of RNase A. The CCMV standards prepared by adding 10 μL of CCMV at concentrations of 93 (1), 69.8 (2), and 46.5 (3) ng/μL, respectively, correspond to concentrations of RNA (within the virions) of 20, 15, and 10 ng/μL.

The resulting mixture was run in a 1% agarose electrophoresis gel, and ethidium bromide (EtBr) staining revealed no bands associated with free (unpackaged) RNA. Rather, the only band observed was one corresponding to VLPs (FIG. 2B, VLP[-]) which are resistant to RNase digestion (FIG. 2B, VLP[+]). Note that this RNase treatment was sufficient for complete digestion of naked RNA (FIG. 2B, RNA). Comparing the band intensity with lanes containing a set of CCMV standards of known concentration (FIG. 2A) showed that the assembled VLPs contained a concentration of RNA equal to 18 ng/ml. Furthermore, the VLPs were homogeneous (see, however, discussion below TEM data) and had electrophoretic mobilities corresponding to well-formed VLPs.

Figure 3:
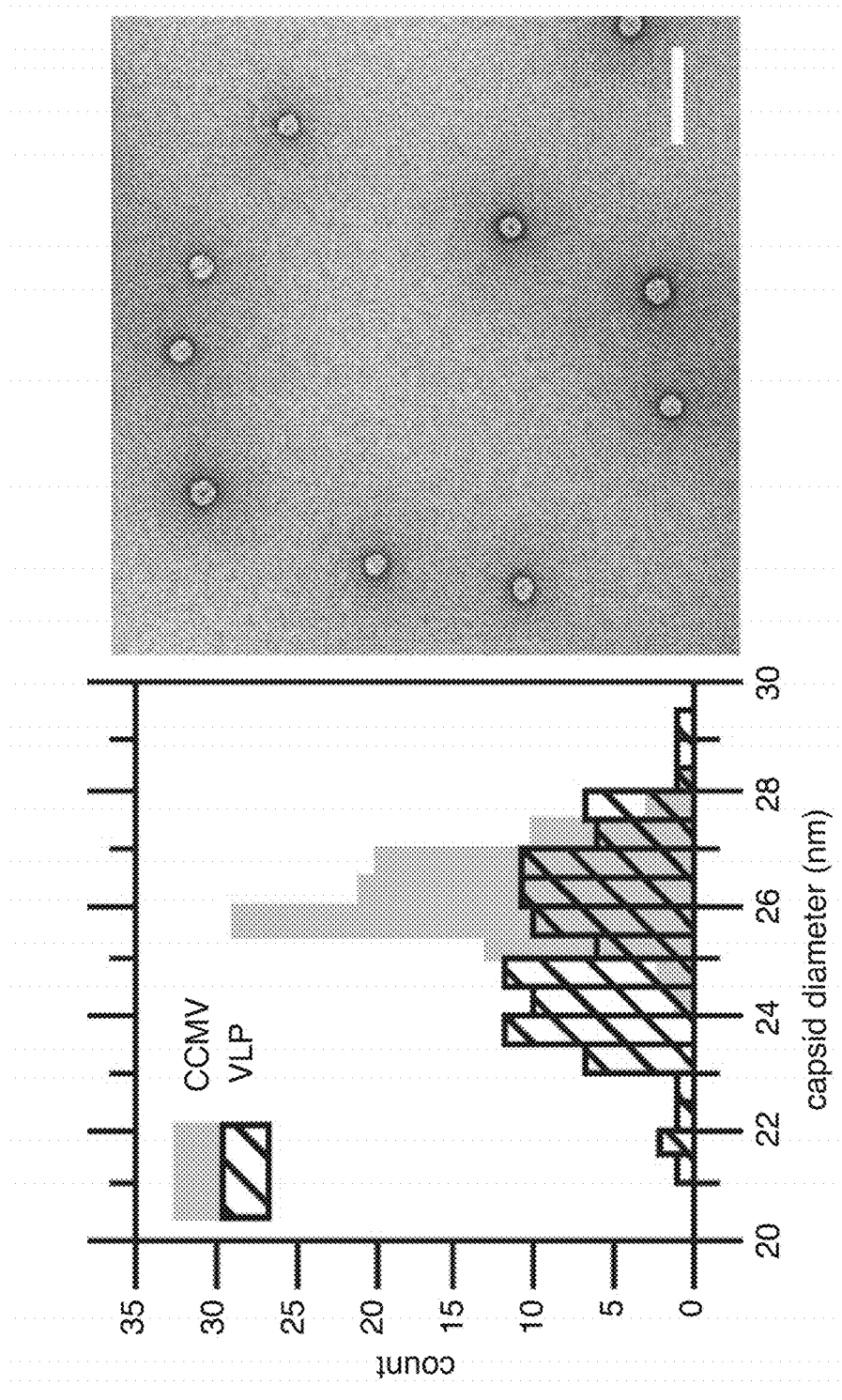
FIG. 3 illustrates the characterization of the VLP size distribution. Left: Distributions of diameters of VLPs (cross-hatched) and of wt CCMV virions (grey). Right: A negative-stain TEM micrograph of the VLPs assembled from CCMV CP+DI[EYFP] RNA. Scale bar=100 nm.

The assembly mix was imaged by negative-stain transmission electron microscopy (TEM). The images showed spherical VLPs (FIG. 3, micrograph) with a distribution of diameters corresponding to roughly equal numbers of "pseudo T=2" and T=3 capsids, overlapping the range of wt CCMV virions (FIG. 3, histogram)—in agreement with what was previously found for packaging of 2000-nt RNA into CCMV VLPs (Cadena-Nava et al., 2012).

CCMV VLPs can Release their RNA Content in the Cytoplasm of Mammalian Cells

Having characterized the plant virus VLPs containing DI[EYFP] RNA, mammalian cells were then transfected with them, using Lipofectamine-2000 (see Methods section). The transfected cells were incubated for 30 min to allow for internalization of the VLPs and for release of their RNA in the cytoplasm. At this point, GP-Rep vector was added at a multiplicity of infection (MOI) of 100 in order to produce a high copy number of EYFP mRNA from DI[EYFP] RNAs that had been released from their CCMV capsids and successfully delivered to the cytoplasm. The intracellular fluorescence signal generated by the subsequent translation of this amplified mRNA into EYFP could then be used to report on the level of VLP delivery and the release of its RNA.

In parallel, equal amounts of the naked DI[EYFP] RNA were transfected by Lipofectamine-2000 into BHK cells under similar conditions. In addition, a sample consisting of "naked" VLPs (i.e., VLPs in final assembly buffer without Lipofectamine) was incubated with BHK cells.

Figure 4:
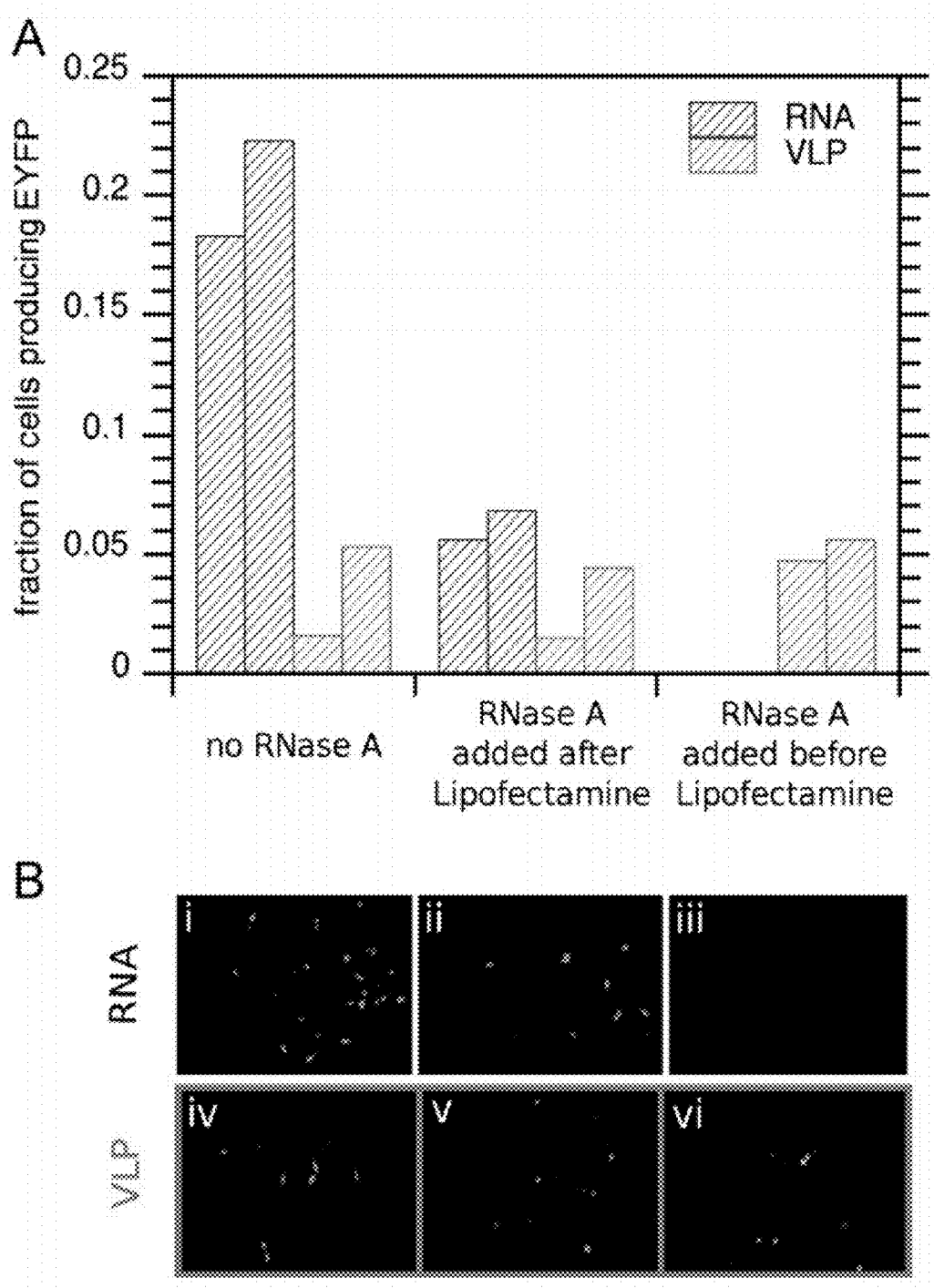
FIG. 4 illustrates that VLPs can release their RNA content into the cytoplasm of transfected cells. (A) Determination of Transduction Efficiency by Flow Cytometry. The left bars show the fractions of positive cells for duplicate sets of transfections of VLPs (red) and naked RNA (black) that were not treated with RNase A. The middle bars show the effect of adding RNase A after mixing with Lipofectamine-2000 (RN2, see Example section). The right bars show the result of incubation with RNase A before addition of Lipofectamine (RN1). From the precision of the cytometry measurements (0.002), an application of the Student t-test shows that the differences between the RNA and VLP measurements are significant with a probability of at least 95%. (B) Fluorescence micrographs of representative fluorescent cell densities for each scenario. Panel (iv) in (B) shows that transfected VLPs can deliver their RNA content into the cytoplasm of mammalian cells, where the RNA is involved in downstream processes, as is the case for the naked RNA control (B(i)). As expected, the naked VLPs overlaid on cells without any Lipofectamine could not transduce cells with EYFP.
Figure 5:
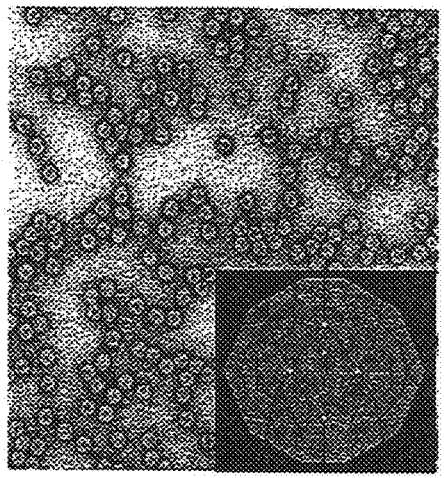
FIG. 5 illustrates the packaging of viruses with single-stranded RNA genomes. The packaging of the genome occurs spontaneously, via self-assembly—no pressure, no work. In one illustrative example, Cowpea Chlorotic Mottle Virus (CCMV) is shown. Each identical 28 nm-capsid consists of 180 copies of one protein, and contains a different molecule of the viral RNA genome—RNA1, RNA2, or RNA3 (+RNA4)—each about 3000 nt long.
Figure 6:
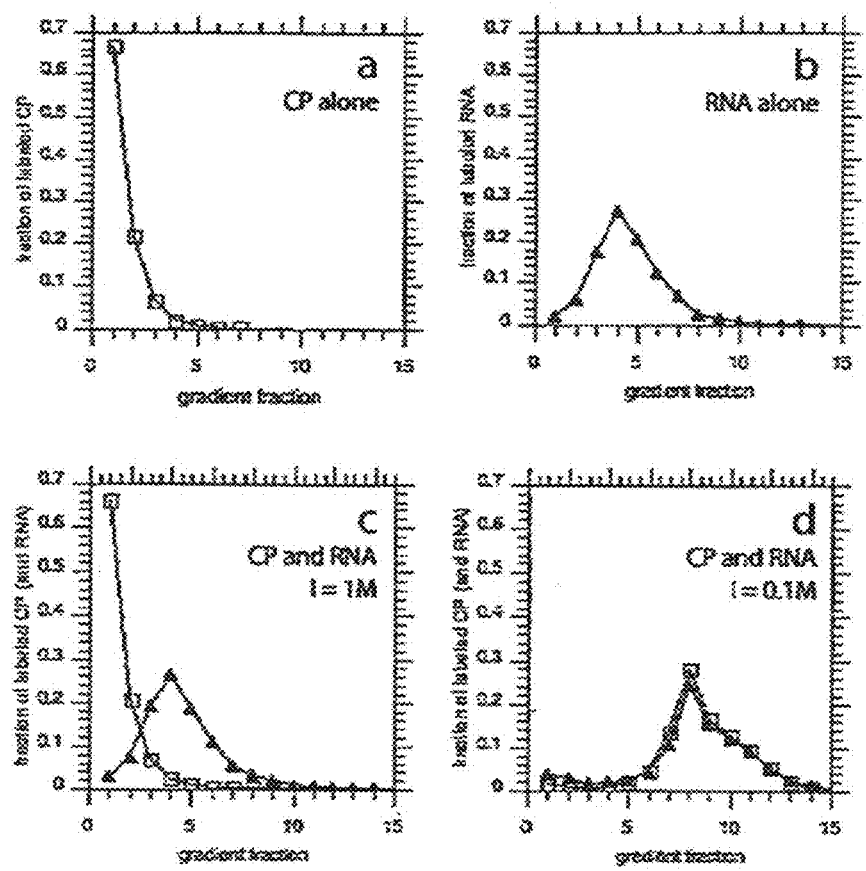
FIG. 6 shows graphs illustrating that super-stoichiometric excess of protein binds in physiological (pH 7, I=0.1M) buffer (the graphs depict experimental results of (a) CP alone, (b) RNA alone, (c) CP and RNA, I=1M, (d) CP and RNA, I=0.1M).
Figure 7:
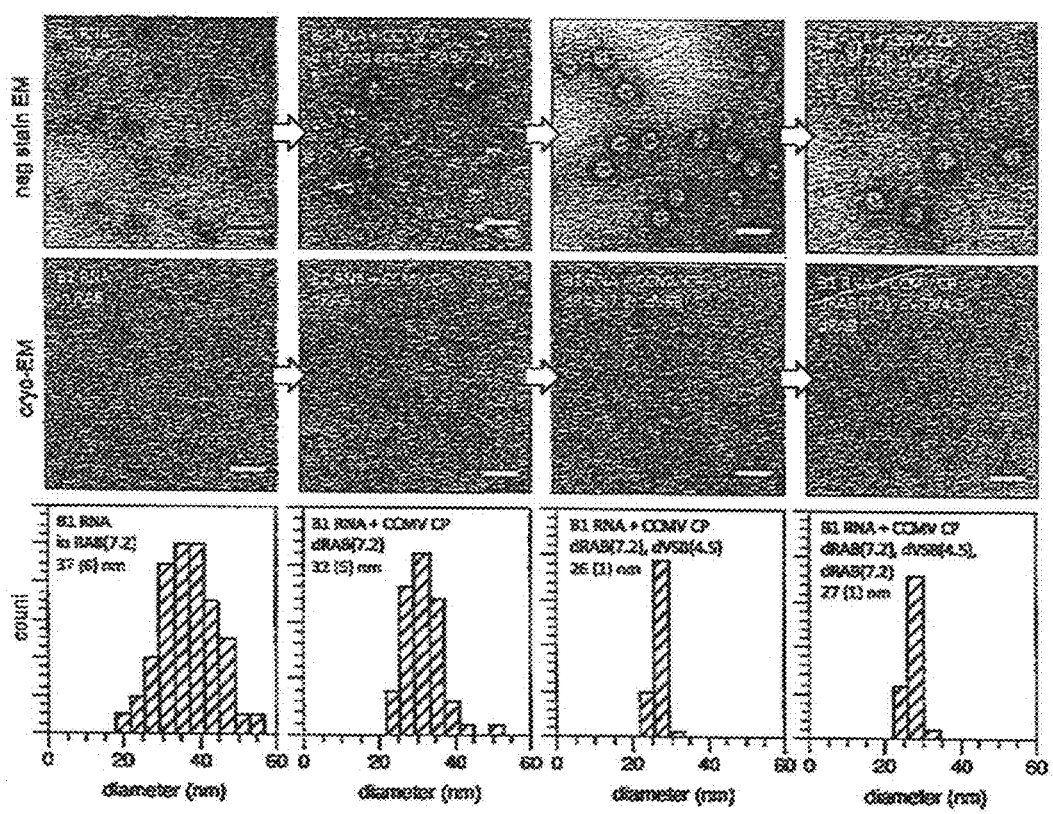
FIG. 7 shows negative stain and cryo-electron microscopy images illustrating that neutral pH assemblies yield protein-decorated RNAs, not VLPs; pH needs to be lowered.
Figure 8:
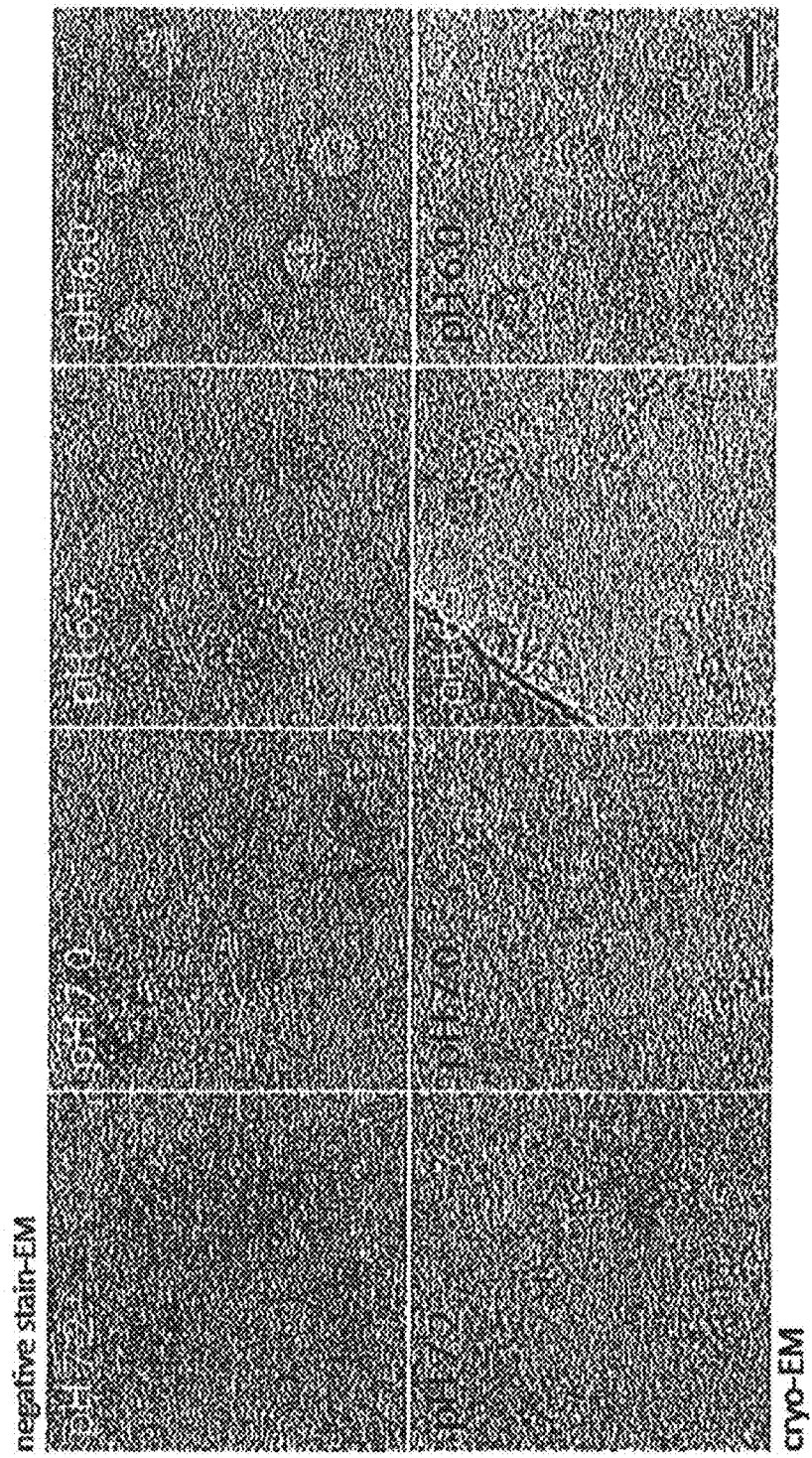
FIG. 8 shows negative stain and cryo-electron microscopy images illustrating that pH lowering "turns on" lateral interactions between bound capsid proteins.

The transfected cells were imaged by fluorescence microscopy to estimate the number of cells positive for EYFP. The number of EYFP-expressing cells was also quantified by flow cytometry; the transduction efficiencies are shown as a function of RNase treatment in FIG. 4A.

The number of fluorescent cells is lower (by a factor of 5) in the case of VLP transfection than for RNA. Two explanations are plausible for this observation: either CCMV VLPs have a lower transfection efficiency than their corresponding RNA content, or not all of the VLPs disassemble to make their RNA content available for transcription, replication and translation. The second scenario—that only about a fifth of the VLPs are releasing their gene cargo, as opposed to 5 times fewer VLPs being transfected than RNAs—is consistent with experiments in which equal numbers of the same VLPs and RNA molecules were manually microinjected—rather than transfected—into the same BHK cells, and the VLPs were found to give rise to a factor of 5 fewer fluorescent cells.

CCMV VLPs Remain Intact Prior to Cell Entry and Protect their RNA Content Against RNase Digestion Two variations on the transfection procedure involving RNase A were carried out in parallel to gain further information about the physical state of the VLPs during transfection. They are referred to as "RN1" and "RN2" and are described below:

RN1: Before the initial equilibration with Lipofectamine-2000, RNase A was added to both the packaged and naked RNA samples. This digestion step was designed to remove all naked full-length RNAs from solution and ensure that any transduction activity (reported by EYFP production) generated by the VLPs did not come from trace amounts of unpackaged RNA or from RNA that escaped from the VLPs during transfection. Essentially identical transduction efficiencies for VLPs with and without RNase digestion was observed (FIG. 4B iv and vi), indicating that unpackaged RNA was not involved. The complete absence of EYFP transduction in the digested naked RNA sample (see FIG. 4Biii) was also observed, confirming that the concentration of RNase A used was adequate for complete removal of all naked full-length RNA in solution.

RN2: RNase A was added immediately after the addition of Lipofectamine. This digestion step was designed to test whether Lipofectamine-2000 is capable of protecting unpackaged RNA against RNase A digestion. The results show (see FIG. 4) that adding RNase A at this step of the transfection procedure results in a large attenuation of the transduction activity of the naked RNA while having no effect on that of the VLPs, indicating again that VLPs are being transfected as intact capsids.

The intact state of the plant viral capsids, even after RNase treatment in the absence and presence of Lipofectamine, is only one measure of their robustness. Another is their "shelf-life" between synthesis and transfection: in the experiments described above, for example, the VLPs were left for 1 week at 4° C. before being subjected to RNase treatment and transfection.

Conclusions

It has now been shown that plant VLPs formed in vitro from CCMV capsid protein and several-thousand-nt-long RNA: (1) are resistant to RNase; (2) can be transfected into mammalian cells, and (3) disassemble in these cells, resulting in the expression of the target transgene.

This demonstration establishes that plant virus capsids—here CCMV—are capable of protecting their RNA contents outside the cell, and yet making them available in the intracellular environment of mammalian cells. The CP as well as the RNA of a super-family of plus-strand RNA viruses like CCMV and SINV have been chosen—as opposed to minus-strand or retro RNA viruses—in order to avoid the complications of needing to package directly the delicate RNA-dependent RNA polymerase or reverse transcriptase proteins themselves. Further, with plus-strand viruses, all of the nucleic acid replication takes place in the cytoplasm rather than requiring trafficking of RNA into and out of the host cell nucleus. In addition, utilizing the DI[EYFP] RNA in conjunction with GP-Rep vector infection, we are able to exploit the powerful messenger RNA amplification scheme unique to plus-strand RNA viruses (Strauss and Strauss, 1994; Frolov et al., 1996). More explicitly, upon release from its VLP each DI[EYFP] RNA is not only transcribed into EYFP mRNA suitable for translation, but is also replicated by the RNA-dependent RNA polymerase (supplied by the GP-Rep vector) into many copies, each of which can in turn be transcribed again and used in the translation of the reporter EYFP. It is this enhancement that significantly increases the sensitivity for detecting RNA release from the VLPs in the cytoplasm.

These studies were undertaken to demonstrate that nucleocapsids of plant viral capsid protein—prepared as nuclease-resistant closed shells—are capable of making available heterologous RNA content to mammalian cells, and that RNA genes in this form can be expressed. Disassembly of these VLPs is most likely driven by their binding to ribosomes, as has been demonstrated in studies of bromoviruses (Roenhorst et al., 1989) and alphaviruses (Singh and Helenius, 1992). Here transfection of the VLPs is used to provide a "proof of principle" demonstration of RNA release and expression. The results of this work can now be directly combined with functionalization of the capsid protein for targeting and uptake by mammalian cells (Destito et al., 2007; Gonzales et al., 2009; Yildiz et al., 2011; Steinmetz, 2010; Wu et al., 2012; Koudelka et al., 2009; Jung et al., 2011; Lockney et al., 2011), thereby facilitating the use of reconstituted plant viral capsids for gene delivery.

Materials and Methods

Constructs and Reagents

Di[EYFP]-RNA

The DI[EYFP] construct was the result of (1) deletion of the region spanning BamHI and BspEI restriction sites on the NS ORF of SINV cDNA, and (2) replacement of the S ORF with nuclear EYFP ORF, using standard molecular biology protocols. The resulting plasmid—after linearization—was used as the template for in vitro transcription using Ambion Sp6 mMessage mMachine in vitro transcription kit. The RNA was purified with a Qiagen mini RNeasy kit, and quantified by UV absorption at 260 nm.

GP-Rep Vector

First, two constructs, GP-Rep and DHBB plasmids, were prepared: GP-Rep was made by deleting the CP gene from the structural ORF in the SINV cDNA while DHBB was made by deleting the region between BamHI and BspEI sites on the NS ORF of SINV cDNA. These constructs were made into corresponding RNA transcripts, using in vitro transcription (see above). Next, the two RNAs were cotransfected into BHK cells using electroporation protocol. The vector particles were harvested from the medium on top of transfected cells after 24 h.

CCMV CP Purification

CCMV was purified from infected California cowpea plant (*Vigna ungiculata* cv BlackEye) (Bancroft, 1970) and CP was isolated as described previously (Cadena-Nava et al., 2011; Annamalai and Rao, 2005). SDS-PAGE and MALDI-TOF were employed to ascertain that the purified protein was intact.

VLP Assembly Reactions

DI[EYFP] RNA was packaged by CCMV CP at a CP:RNA mass ratio of 6.5:1 to ensure complete RNA packaging. Assembly was carried out by mixing CP and RNA in buffer B (1 M NaCl, 20 mM Tris-HCl pH 7.2, 1 mM EDTA, 1 mM DTT and 1 mM PMSF), followed by dialysis against RNA assembly buffer (RAB: 50 mM NaCl, 10 mM KCl, 5 mM $MgCl_2$, 1 mM DTT, 50 mM Tris-HCl pH 7.2) for 4 h, followed by dialysis against virus buffer (VB: 0.1M sodium acetate, 1 mM EDTA, pH4.8) for 16 h, all at 4° C. Free (excess) CP was removed by washing the sample with VB in a 100 kDa Amicon centrifugal filtration unit at 3000 G at 4° C.

Electron Microscopy Characterization of VLPs

A 6 μl aliquot of the final assembly mixture was applied to a glow-discharged copper grid (400-mesh) that previously had been coated with Parlodion and carbon. The mix was spread onto the grid for 1 min, blotted with Whatman filter paper and then stained with 6 μL of 1% uranyl acetate for 1 min. Excess stain was removed by blotting with filter paper. The samples were stored overnight in a desiccator and analyzed with a JEM 1200-EX transmission electron microscope operated at 80 keV and equipped with a wide-angle (topmount) BioScan 600 W 1×1 $K^2$ pixel digital camera. The reported average diameter of VLPs is that of the geometric mean of two orthogonal measurements of the capsids obtained with ImageJ (U.S. National Institutes of Health) software from recorded images.

Preparation of BHK Cell Culture

Prior to transfection, BHK-21 cells were grown as monolayers on 6-well plates at37° C. in a $CO_2$ incubator. EMEM (ATCC) supplied with 10% (v/v) FCS and Penicillin-streptomycin was used to grow and maintain cells.

Lipofectamine Transfections

Monolayers of BHK cells were grown on six-well plates to 90% confluence. Transfection with Lipofectamine-2000 was carried out following a standard protocol normally used for the transfection of nucleic acids. Briefly, the protocol consisted of the following (5) steps:

(1) An aliquot of VLPs (or naked RNA) containing 1 μg of DI[EYFP] RNA was diluted into Opti-MEM to 300 μl for each transfection. Similarly, 3 μl of Lipofectamine-2000 was diluted into 300 μl Opti-MEM and the dilutions were incubated at room temperature for 5 min.

(2) The two diluted reagents were mixed and (RNA/VLP+Lipofectamine) complexes were allowed to form by incubating at room temperature for 30 min.

(3) The cells were washed with 1× nuclease-free PBS before overlaying the transfectant onto the cells, followed by incubation at 37° C. in a $CO_2$ incubator with occasional shaking to distribute the transfectant evenly on the cells.

(4) After 30 min of incubation, a 150-mL aliquot of GP-Rep vector at an MOI of >100 was added to the cells in order to supply the replication machinery necessary for EYFP production. Longer incubation times did not enhance the transduction yield.

(5) After 4 h the transfectant/inoculums was removed and the cells were gently washed twice with pre-warmed 1×PBS and 1 ml of 2% FCS medium was overlaid on the cells. The cells were left overnight at 37° C. in a $CO_2$ incubator.

RNaseA Assays

All RNase A digestion steps were carried out using 0.2 ng/u1 RNase A for 30 min at room temperature. For digestions that were performed during the transfection protocol (i.e. scenarios RN1 and RN2), this concentration of RNase A was maintained throughout each subsequent step of the protocol. These conditions were found to be sufficient to remove all full-length RNA band intensity from the agarose gel assay (FIG. 2B, RNA panel) as well as completely destroy the transfection efficiency of naked RNA by Lipofectamine-2000 (FIGS. 4A and 4Biii, vi).

Flow Cytometry

Twenty-four hour post-transfection, the cells were washed with 1×PBS, trypsinized, and resuspended in 1×PBS buffer with 2% FCS at a density of $3\times10^6$ cells/ml. Analysis was performed using a Becton Dickinson SORP BD LSRII Analytic Flow Cytometer equipped with a 488-nm blue laser for excitation of EYFP. Yellow-green YFP fluorescence was collected after a 530/30 bandpass filter. FACSDIVa software was used to control the parameters during the run and to analyze collected data.

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

REFERENCES

Allison R. F., Janda M., Ahlquist P., 1989. Sequence of cowpea chlorotic mottle virus RNAs 2 and 3 and evidence of a recombination event during bromovirus evolution. Virology 172 (1), 321-330.

Annamalai, P., Rao, A. L. N., 2005. Dispensability of 3'tRNA-Like Sequence for packaging Cowpea Chlorotic Mottle virus genomic RNAs. Virology 332, 650-658.

Ashley, C. E., Carnes, E. C., Phillips, G. K., Durfee, P. N., Buley, M. D., Lino, C. A., Padilla, D. P., Phillips, B., Carter, M. B., Willman, C. L., Brinker, C. J., Caldeira, J., Chackerian, B., Wharton, W., Peabody, D. S., 2011. Cell-specific delivery of diverse cargos by bacteriophage MS2 virus-like particles. ACS Nano 5, 5729-5745.

Bancroft, J. B., Hiebert, E., 1967. Formation of an infectious nucleoprotein from protein and nucleic acid isolated from a small spherical virus. Virology 32, 354-356.

Bancroft, J. B., Hiebert, E., Bracker, C. E., 1969. The effects of various polyanions on shell formation of some spherical viruses. Virology 39, 924-930.

Bancroft, J. B., 1970. The self-assembly of spherical plant viruses. Adv. Virus Res. 16, 99-134.

Brasch, M., de La Escosura, A., Ma, Y., Uetrecht, C., Heck, A. J. R., Tones, T., Cornelissen, J. J. L. M., 2011. Encapsulation of phthalocyanine supramolecular stacks into virus-like particles. J. Am. Chem. Soc. 133, 6878-6881.

Brasch, B., Cornelissen, J. J. L. M., 2012. Relativesizeselectionofaconjugated polyelectrolyteinvirus-likeproteinstructures. Chem. Commun. 48, 1446-1448.

Cadena-Nava, R. D., Hu, Y., Garmann, R. F., Ng, B., Zelikin, A. N., Knobler, C. M., Gelbart, W. M., 2011. Exploiting fluorescent polymers to probe the self-assembly of virus-like particles. J. Phys. Chem. B 115, 2386-2393.

Cadena-Nava, R. D., Comas-Garcia, M., Garmann, R. F., Rao, A. L. N., Knobler, C. M., Gelbart, W. M., 2012. Self-assembly of viral capsid protein and RNA molecules of different sizes: Requirement for a specific high protein/RNA mass ratio. J. Virol. 86, 3318-3326.

Chang, C. B., Knobler, C. M., Gelbart, W. M., Mason, T. G., 2008. Curvature dependence of viral protein structures on encapsidated nanoemulsion droplets. ACS Nano 2, 281-286.

Chen, C., Daniel, M. C., Quinkert, Z. T., De, M., Stein, B., Bowman, V. D., Chipman, P. R., Rotello, V. M., Kao, C. C., Dragnea, B., 2006. Nanoparticle-templated assembly of viral protein cages. Nano Lett. 6, 611-615.

Chen, C.-Y., Lin, C.-Y., Chen, G.-Y., Hu, Y.-C., 2011. Baculovirus as a gene delivery vector: Recent understandings of molecular alterations in transduced cells and latest applications. Biotechnol. Adv. 29, 618-631.

Cheng, F., Mukhopadhyay, S., 2011. Generating virus-like particles with in vitro assembled cores. Virology 413, 153-160.

Destito, G., Yeh, R., Rae, C. S., Finn, M. G., Manchester, M., 2007. Folic acid-mediated targeting of cowpea mosaic virus particles to tumor cells. Chem. Biol. 14, 1152-1162.

Douglas, T., Young, M., 1998. Host—guest encapsulation of materials by assembled virus protein cages. Nature 393, 152-155.

Fox, J. M., Wang, G., Speir, J. A., Olson, N. H., Johnson, J. E., Baker, T. S., Young, M. J., 1998. Comparison of the native CCMV virion with in vitro assembled CCMV virions by cryoelectron microscopy and image reconstruction. Virology 244, 212-218.

Frolov, I., Hoffman, T. A., Pragai, B. M., Dryga, S. A., Huang, H. V., Schlesinger, S., Rice, C. M., 1996. Alpha virus-based expression vectors: Strategies and applications. Proc. Natl. Acad. Sci. (USA) 93, 11371-11377.

Goelet P., Lomonossoff G. P., Butler P. J. G. Akam M. E., Gait M. J., Karn J. 1982. Nucleotide sequence of tobacco mosaic virus RNA. Proc. Natl. Acad. Sci. USA, 79, 5818-5822.

Goicochea, N. L., De, M., Rotello, V. M., Mukhopadhyay, S., Dragnea, B., 2007. Core-like particles of an enveloped animal virus can self-assemble efficiently on artificial templates. Nano Lett. 7, 2281-2290.

Gonzales, M. J., Plummer, E. M., Rae, C. S., Manchester, M. J., 2009. Interaction of Cowpea Mosaic Virus (CPMV) nanoparticles with antigen presenting cells in vitro and in vivo. PLoS One 4, e7981.

Hiebert, E., Bancroft, J. B., Bracker, C. E., 1968. The assembly in vitro of some small spherical viruses, hybrid viruses, and other nucleoproteins. Virology 34, 492-508.

Hu, Y., Zandi, R., Anavitarte, A., Knobler, C. M., Gelbart, W. M., 2008. Packaging of a polymer by a viral capsid: The interplay between polymer length and capsid size. Biophys. J. 94, 1428-1436.

Jung, B., Rao, A. L. N., Anvari, B., 2011. Optical nanoconstructs composed of genome-depleted brome mosaic virus doped with a near infrared chomophore for potential biomedical applications. ACS Nano 5, 1243-1252.

Koudelka, K. J., Destito, G., Plummer, E. M., Trauger, S. A., Siuzdak, G., Manchester, M., 2009. Endothelial targeting of Cowpea Mosaic Virus (CPMV) via Surface vimentin. PLoS Pathog 5, e1000417/1-10.

Lavillette, D., Russell, S. J., Cosset, F. L., 2001. Retargeting gene delivery using surface-engineered retroviral vector particles. Curr. Opin. Biotech. 12, 461-466.

Li, L., Wang, L., Xiao, R., Zhu, G., Li, Y., Liu, C., Yang, R., Tang, Z., Li, J., Huang, W., Chen, L., Zheng, X., He, Y., Tan, J., 2012. The invasion of tobacco mosaic virus RNA induces endoplasmic reticulum stress-related autophagy in HeLa cells. Biosci. Rep. 32, 171-184.

Lockney, D. M., Guenther, R. N., Loo, L., Overton, W., Antonelli, R., Clark, J, Hu, M., Luft, C., Lommel, S. A., Franzen, S., 2011. The RCNMV capsid as a multifunctional cell targeting plant viral nanoparticle. Bioconjugate Chem. 22, 67-73.

Mahraj, P. D., et al., 2014. Nanoparticle encapsidation of Flock House virus by auto assembly of Tobacco Mosaic virus coat protein. Int. J. Mol. Sci. 15, 1-16 manuscripts.

Minten, I. J., Hendriks, L. J. A., Nolte, R. J. M., Cornelissen, J. J. L. M., 2009. Controlled encapsulation of multiple proteins in virus capsids. J. Am. Chem. Soc. 131, 17771-17773.

Mukhopadhyay, S., Chipman, P. R., Hong, E. M., Kuhn, R. J., Rossmann, M. G., 2002. In vitro-assembled alphavirus core-like particles maintain a structure similar to that of nucleocapsid cores in mature virus. J. Virol. 76, 11128-11132.

Rao, A. L. N., 2006. Genome packaging by spherical plant RNA viruses. Annu Rev. Phytopathol. 44, 61-87.

Roenhorst, J. W., Verduin, B. J. M., Goldbach, R. W., 1989. Virus-ribosome complexes from cell-free translation systems supplemented with cow pea chlorotic mottle virus particles. Virology 168, 138-146.

Sainsbury, F., Lomonossoff, G. P., 2008. Extremely high-level and rapid transient protein production in plants without the use of viral replication. Plant Physiol. 148, 1212-1218.

Schaffer, D. V., Koerber, J. T., Lim, K., 2008. Molecular engineering of viral gene delivery vehicles. Annu Rev. Biomed. Eng. 10, 169-194.

Singh, L., Helenius, A., 1992. Role of ribosomes in Semliki forest virus nucleocapsid uncoating. J. Virol. 66, 7049-7058.

Smith, M. L., et al., 2007. Assembly of trans-encapsidated recombinant viral vectors engineered from Tobacco mosaic virus and Semliki Forest virus and their evaluation as immunogens. Virology 358, 321-333.

Soong, N. W., Nomura, L., Pekrun, K., Reed, M., Sheppard, L., 2000. Molecular breeding of viruses. Nat. Genet. 25, 436-439.

Steinmetz, N. F., 2010. Viral nanoparticles as platforms for next-generation therapeutics and imaging devices. Nanomed. 6, 634-641.

Strauss, J. H., Strauss, E. G., 1994. The Alpha viruses: Gene expression, replication, and evolution. Microbiol. Rev. 58, 491-562.

Tellinghuisen, T. L., Hamburger, A. E., Fisher, B. R., Ostendorp, R., Kuhn, R. J., 1999. In vitro assembly of alpha virus cores by using nucleocapsid protein expressed in *E. coli*. J. Virol. 73, 5309-5319.

U.S. Pat. Nos. 7,939,318 and 7,084,256.

U.S. Patent Publication Nos. 2002/0187952, 2003/0035807, 2003/0039659, 2003/0044417, 2003/0044420, 2003/0124091, 2004/0033585, 2004/0170606, 2005/0282263, 2006/0188991, and 2006/0018900.

Wengler, G., Boege, U., Wengler, G., Bischoff, H., Wahn, K., 1982. The core protein of the Alpha virus Sindbis virus assembles into core-like nucleoproteins with the viral genome RNA and with other single-stranded nucleic acids in vitro. Virology 118, 401-410.

Wu, Z., Chen, K., Yildiz, I., Dirksen, A., Fischer, R., Dawson, P. E., Steinmetz, N. F., 2012. Development of viral nanoparticles for efficient intracellular delivery. Nanoscale 4, 3567-3576.

Yildiz, I., Shukla, S., Steinmetz, N. F., 2011. Applications of viral nanoparticles in medicine. Curr. Opin. Biotechnol. 22, 901-908.

Zhao, X., Fox, J. M., Olson, N. H., Baker, T. S., Young, M. J., 1995. In vitro assembly of cowpea chlorotic mottle virus from coat protein expressed in *Escherichia coli* and in vitro-transcribed viral cDNA. Virology 207, 486-494.

Capsid Protein Cowpea Chlorotic Mottle Virus
Accession P03601

(SEQ ID NO: 1)

```
MSTVGTGKLTRAQRRAAARKNKRNTRVVQPVIVEPIASGQGKAIKAWT

GYSVSKWTASCAAAEAKVTSAITISLPNELSSERNKQLKVGRVLLWLG

LLPSVSGTVKSCVTETQTTAAASFQVALAVADNSKDVVAAMYPEAFKG

ITLEQLTADLTIYLYSSAALTEGDVIVHLEVEHVRPTFDDSFTPVY
```

See, e.g. Allison et al., Virology 172 (1), 321-330 (1989)

Tobacco Mosaic Virus Origin of Assembly (SEQ ID NO: 2)

```
guuugagaga gaagauuaca aacgugagag acggagggcc cauggaacuu acagaagaag ucguugauga guucauggaa gaugucccua ugucgaucag gcuugcaaag uuucgaucuc gaaccgg
```

See, e.g. Goelet et al., Proc. Natl. Acad. Sci. USA (79) 5818-5822 (1982)

CONCLUSION

This concludes the description of the illustrative embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

The invention claimed is:

1. A method of delivering a ribonucleic acid into the cytoplasm of a mammalian cell, the method comprising:
   (a) combining the mammalian cell with a composition comprising a ribonucleic acid enveloped by a cowpea chlorotic mottle virus capsid; wherein:
   the composition is formed by combining cowpea chlorotic mottle virus capsid protein and ribonucleic acid in vitro, wherein the relative amounts of cowpea chlorotic mottle virus capsid protein and ribonucleic acid are selected so that there are at least 10 cowpea chlorotic mottle virus capsid proteins for every 100 nucleotides of ribonucleic acid length;
   the ribonucleic acid is at least 100 nucleotides in length;
   the ribonucleic acid is not a cowpea chlorotic mottle virus ribonucleic acid; and
   the cowpea chlorotic mottle virus capsid protein envelops the ribonucleic acid so as to inhibit RNAse nuclease degradation of the ribonucleic acid; and
   (b) allowing the cowpea chlorotic mottle virus capsid to contact the mammalian cell and deliver the ribonucleic acid into the cytoplasm of a mammalian cell.

2. The method of claim 1, wherein the ribonucleic acid encodes at least one polypeptide that is expressed in the mammalian cell following delivery of the ribonucleic acid into the cytoplasm of the mammalian cell.

3. The method of claim 2, wherein the ribonucleic acid encodes a RNA-dependent RNA polymerase.

4. The method of claim 2, wherein the ribonucleic acid encodes a polypeptide selected for its ability to facilitate imaging of the mammalian cell.

5. The method of claim 2, wherein the ribonucleic acid encodes a polypeptide useful in a therapeutic regimen.

6. The method of claim 1, wherein the cowpea chlorotic mottle virus capsid protein is coupled to a polypeptide selected for its ability to bind a molecule expressed on the surface of the mammalian cell.

7. The method of claim 1, wherein the mammalian cell is a cancer cell.

8. The method of claim 1, wherein the ribonucleic acid does not include a signal sequence that modulates packaging of the ribonucleic acid by the capsid proteins.

* * * * *